United States Patent
Remes

(10) Patent No.: US 10,139,379 B2
(45) Date of Patent: Nov. 27, 2018

(54) METHODS FOR OPTIMIZING MASS SPECTROMETER PARAMETERS

(71) Applicant: Thermo Finnigan LLC, San Jose, CA (US)

(72) Inventor: Philip M. Remes, San Jose, CA (US)

(73) Assignee: THERMO FINNIGAN LLC, San Jose, CA (US)

(*) Notice: Subject to any disclaimer, the term of this patent is extended or adjusted under 35 U.S.C. 154(b) by 124 days.

(21) Appl. No.: 15/189,953

(22) Filed: Jun. 22, 2016

(65) Prior Publication Data
US 2017/0370889 A1  Dec. 28, 2017

(51) Int. Cl.
| | |
|---|---|
| *G01N 30/86* | (2006.01) |
| *G01N 30/72* | (2006.01) |
| *G06F 19/00* | (2018.01) |
| *H01J 49/00* | (2006.01) |

(52) U.S. Cl.
CPC ..... *G01N 30/8658* (2013.01); *G01N 30/7233* (2013.01); *G01N 30/8637* (2013.01); *G01N 30/8693* (2013.01); *G06F 19/703* (2013.01); *H01J 49/0031* (2013.01)

(58) Field of Classification Search
CPC ................ G01N 30/8658; G01N 30/7233
USPC ..................................................... 702/189
See application file for complete search history.

(56) References Cited

U.S. PATENT DOCUMENTS

| | | | |
|---|---|---|---|
| 7,541,575 B2 | 6/2009 | Lock et al. | |
| 7,983,852 B2* | 7/2011 | Wright | G01N 30/8624 702/32 |
| 8,704,164 B2* | 4/2014 | Bateman | H01J 49/0031 250/281 |
| 2011/0266426 A1* | 11/2011 | Schwartz | H01J 49/0009 250/252.1 |

(Continued)

FOREIGN PATENT DOCUMENTS

EP  2775509 A2  9/2014

OTHER PUBLICATIONS

Press et al., "Chapter 10. Minimization or Maximization of Functions", in: "Numerical Recipes in C++—The Art of Scientific Computing, 2nd ed.", 2002, Cambridge University Press, pp. 394-454.

*Primary Examiner* — Ricky Ngon
(74) *Attorney, Agent, or Firm* — Thomas F. Cooney

(57) ABSTRACT

A method for determining optimal values of a mass spectral operating parameter for mass spectral analysis of each of a plurality of compounds comprises: acquiring a plurality of mass spectral measurements of each of at least one characteristic ion species of each respective compound during its introduction into a mass spectrometer while a quantity of each introduced compound varies with time wherein, for each characteristic ion species, the operational parameter is caused to vary between successive mass spectral measurements of the said species; calculating, for each characteristic ion species, a corrected intensity of at least a portion of the plurality of mass spectral measurements of said each spe- (Continued)

cies, based on a best-fit synthetic model curve that relates to the time variation of the respective corresponding compound; and determining the optimal values of the operating parameter from analyses of variation of the corrected intensities with respect to the operational parameter variation.

11 Claims, 16 Drawing Sheets

(56) References Cited

U.S. PATENT DOCUMENTS

| | | | |
|---|---|---|---|
| 2012/0049056 A1* | 3/2012 | Zabrouskov | H01J 49/0045 250/282 |
| 2012/0158318 A1 | 6/2012 | Wright | |
| 2013/0105682 A1* | 5/2013 | Geromanos | H01J 49/005 250/282 |
| 2013/0105684 A1* | 5/2013 | Louette | B82Y 15/00 250/282 |
| 2013/0214146 A1* | 8/2013 | Okumura | H01J 49/0009 250/281 |
| 2014/0005970 A1* | 1/2014 | Richardson | H01J 49/0036 702/104 |
| 2014/0014833 A1* | 1/2014 | Sekiya | G01N 30/8651 250/288 |
| 2014/0138537 A1 | 5/2014 | Grothe, Jr. et al. | |
| 2014/0326875 A1* | 11/2014 | Asano | H01J 49/005 250/288 |
| 2015/0102219 A1* | 4/2015 | Yamamoto | H01J 49/005 250/290 |
| 2016/0363569 A1 | 12/2016 | Walsh et al. | |

* cited by examiner

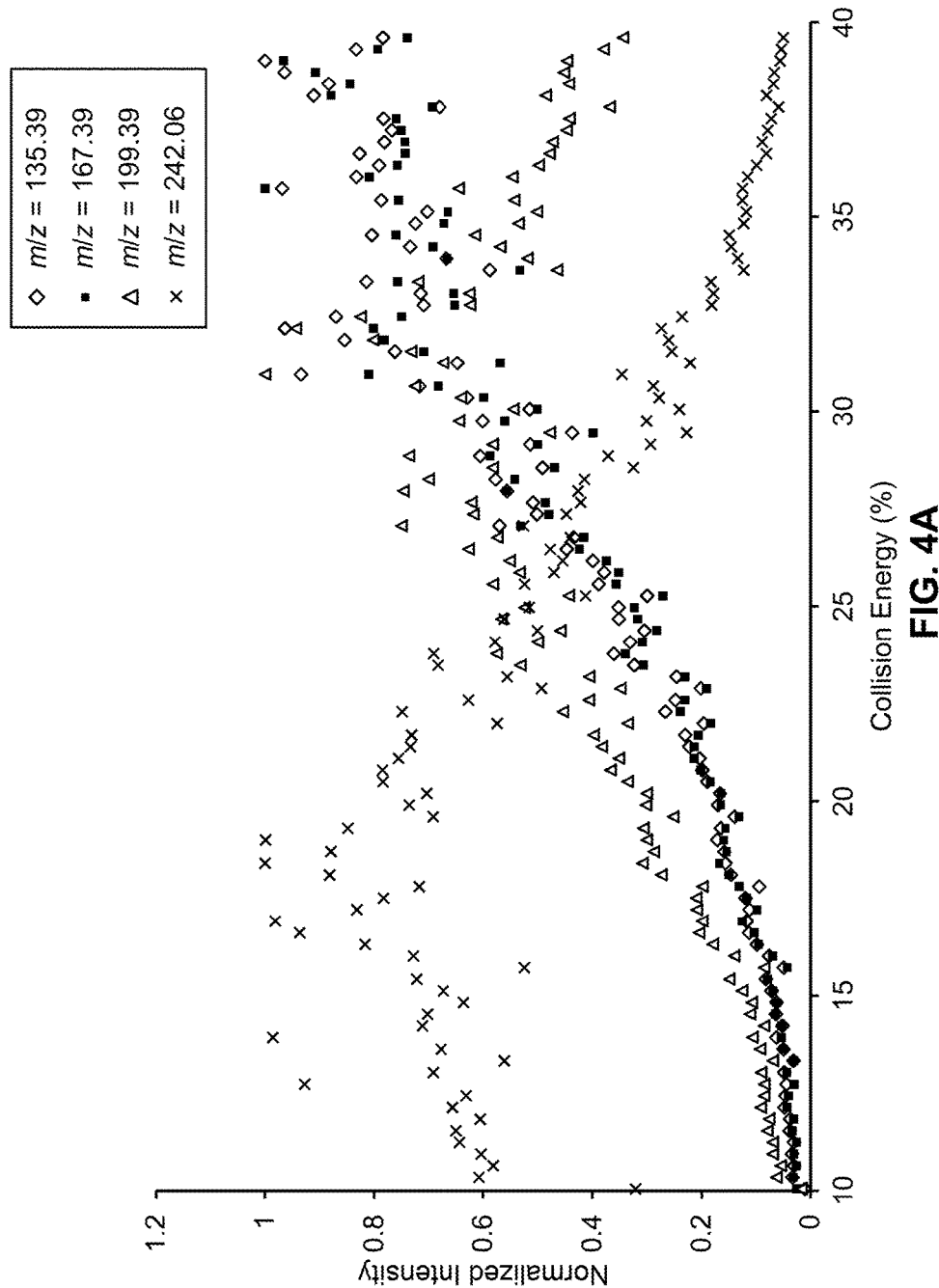

METHODS FOR OPTIMIZING MASS SPECTROMETER PARAMETERS

FIELD OF THE INVENTION

This invention relates, in general, to methods of operating mass spectrometers, and relates, in particular, to methods of optimizing mass spectrometer operating parameters.

BACKGROUND OF THE INVENTION

Mass spectrometry (MS) and, in particular, tandem mass spectrometry (MS/MS) coupled with a chromatographic separation technique such as liquid chromatography (LC) or gas chromatography (GC) has found widespread application in the analytical sciences due its high sensitivity, selectivity, and throughput. Commercial instruments typically employ calibrations that help to optimize various parameters such as MS/MS collision energy as a function of characteristics of anticipated analytes such as mass and charge. Each such calibration is only highly successful for a narrow class of analytes, such as peptides. For classes of analytes other than the class for which a particular calibration was developed, the calibration may be much less successful, due to the disparate compound structures and cleavable bonds that may be encountered. Thus, for analysis of many species such as drug compounds, pesticides, and metabolites, targeted methods must be painstakingly developed through a process of manual optimization for each class of compound or more commonly for each individual compound. A typical pesticide assay of 300 compounds, for example, is conventionally developed by producing sets of mixtures of ~10 compounds each. Each of the 30 mixtures is separately infused with a syringe pump into a mass spectrometer, and the mass spectrometer parameters of interest are optimized for each compound in the mixture. Even when performed by a trained analyst, this process requires a time duration on the order of 1-2 weeks to complete. Strides are being made towards automating parts of this process; for example, an autosampler can be used to infuse the compounds. Nonetheless, the key limitation has not yet been addressed, which is the need to create many subsets of compounds and infuse each one separately. One important problem that must be overcome in order to address this limitation is that the current optimization techniques are not able to account for analyte flux that varies with time; as a result, the improved efficiency that hypothetically could be achieved by LC separation is not available for such optimization programs. The present inventor has thus recognized a need in the mass spectrometry art for development of more-efficient methods of optimizing mass spectrometer operational parameters that may be employed on chromatography fractions as they elute. This disclosure provides methods that remedy this problem, enabling MS parameter optimization on mixtures of large numbers of compounds in a shorter amount of time than is required using conventional techniques.

SUMMARY OF THE INVENTION

In order to address the above-noted need in the art, the present invention provides methods for optimizing mass spectrometer operating parameters that can be applied to situations in which analyte concentrations are not constant as a function of time. Such methods are useful, as but one example, in the context of automated compound optimization for assays containing large numbers of uncharacterized species, a procedure which conventionally requires that analyte concentrations are constant, conventionally precluding the use of a chromatograph or other fractionation apparatus coupled to the inlet of the mass spectrometer. By removing the effect of the time varying concentration, optimization of parameters can be performed on analytes eluting from a chromatographic column or other fractionation apparatus, thus dramatically decreasing the time and effort required for compound optimization.

A new workflow for creating the best set of optimization experiments from a given set of compounds is also described, which accounts for the time density of analytes and the number of experiments required to perform an optimization. It is to be noted that, unless otherwise indicated, the term "experiment", as used throughout this document, refers to the procedure of acquiring a set of one or mass spectra of ions of a particular plurality of sample compounds within a fluid stream that is provided to a mass spectrometer, wherein the acquiring of the set of mass spectra is performed during the providing of the fluid stream. If the mass spectra are acquired by a quadrupole mass analyzer (a quadrupole mass filter or quadrupole trap) or other scanning-type apparatus, then each such mass spectrum may be referred to as a "scan". The fluid stream may comprise an effluent (that is, an eluate) from a liquid or gas chromatograph, in which case the experiment may be described as an LCMS (liquid chromatography mass spectrometry) experiment or GCMS (liquid chromatography mass spectrometry) experiment, respectively. Alternatively, the fluid stream may comprise an effluent from some other form of fractionation apparatus, such as a capillary electrophoresis apparatus. Since the compounds will be generally be provided sequentially from the chromatograph or other fractionation apparatus to the mass spectrometer, a single LCMS experiment, GCMS experiment or the like will generally encompass the acquisition of many mass spectra in order to detect all compounds of interest during the time period within which the compounds elute. In some other instances, the fluid stream may comprise a flow of a solvent which does not pass through a separation or fractionation apparatus and into which the compounds are injected. The various compounds may be injected into such a solvent stream either separately or in mixtures of two or more compounds and are subsequently introduced into the mass spectrometer without chromatographic separation or other separation or fractionation. In some instances, a number of compounds may arrive at the mass spectrometer simultaneously as a result of co-elution or as a result of simultaneous injection without prior separation. An excessive number of such simultaneously arriving compounds may render the mass spectrometer incapable of acquiring a sufficient quantity of data on each such compound. Such circumstances may necessitate making a choice regarding which of the co-eluting or otherwise simultaneously arriving compounds will be analyzed (i.e., which compounds compose the particular plurality of compounds) in the experiment. Thus, at least one additional experiment may be required in order to obtain mass spectra of other compounds of interest. If the fluid stream is the effluent of a chromatograph, then each additional experiment will include passing a respective portion of the same sample (or a similar sample) through the chromatograph and providing the chromatograph effluent to the mass spectrometer.

In accordance with a first aspect of the present teachings, a method for determining optimal values of a mass spectral operating parameter for use in analyzing each of a plurality of compounds by mass spectrometry is provided, the method comprising: (a) acquiring a plurality of mass spectral measurements of each of at least one characteristic ion species of each respective compound as each said respective compound is introduced into a mass spectrometer and while a respective quantity of each introduced compound varies with time, wherein, for each characteristic ion species, the operational parameter is caused to vary between successive mass spectral measurements of said each characteristic ion species; (b) calculating, for each characteristic ion species, a corrected intensity of at least a portion of the plurality of mass spectral measurements of said each characteristic ion species, based on a best-fit synthetic model curve that relates to the time variation of the respective corresponding compound quantity; and (c) determining the optimal values of the operating parameter from analyses of variation of the corrected intensities with respect to variation of the operational parameter.

According to some embodiments, the characteristic ion species may comprise fragment ions. In such cases, the operational parameter may be an applied collision energy that is applied in order to generate the fragment ions. According to some embodiments, the operational parameter may be a magnitude of a Radio Frequency voltage applied to an ion guiding component of the mass spectrometer. The ion guiding component may be at or immediately adjacent to an ion source of the mass spectrometer.

According to some embodiments, the varying, with time, of the quantity of each said respective compound that is inlet to the mass spectrometer may result from the elution of the compound from a separation or fractionation apparatus, such as a liquid chromatograph, gas chromatograph or the like that is fluidically coupled to the mass spectrometer so as to provide eluate or other effluent to the mass spectrometer. Examples of separation or fractionation techniques that may be employed to produce the time variation of the compounds include, without limitation, liquid chromatography employing column separation (including reversed phase liquid chromatography and hydrophobic interaction chromatography), ion exchange chromatography (ion chromatography), gas chromatography employing column separation, paper chromatography, thin layer chromatography, supercritical fluid chromatography, size-exclusion chromatography, capillary electrochromatography, capillary electrophoresis, etc. For simplicity, all such techniques are referred to herein as falling under the general category of "chromatography" and all such apparatuses are referred to as falling under the general category of "chromatographs".

According to some embodiments, the varying, with time, of the quantity of each said respective compound that is inlet to the mass spectrometer may result from the injection of said each compound into a flow of a solvent that is inlet to the mass spectrometer. In such situations, the passage of the finite quantity of the compound will be observed as a pulse. Simple diffusion within the solvent will cause the pulse to have a maximum concentration approximately at its center and leading and trailing edges of decreasing concentration. Also, the mechanical operation of a sample injector may cause concentration to vary within a pulse. The plurality of compounds may be injected into the flowing solvent by any known apparatus devised for this purpose, such as a known autosampler apparatus. The compounds may be injected individually (i.e., one at a time) or, possibly, as a mixture of mixtures of two or more compounds.

According to some embodiments, each best-fit synthetic model curve may be generated automatically, in the absence of fitting-parameter input by a user. Each best-fit synthetic model curve may be generated based on a signal-versus-time profile of the characteristic ion species determined from the acquiring of the plurality of mass spectral measurements of that ion species, wherein each of several measurements that compose the signal-versus-time profile is obtained with the operational parameter set to a non-variable control state, such that intensity changes observed among the measurements that compose the signal-versus-time profile are known to result from the time variation of the quantity of the respective compound that is inlet to the mass spectrometer. According to some embodiments, the operational parameter may be caused to vary randomly between successive mass spectral measurements of a characteristic ion species during the acquiring of the plurality of mass spectral measurements of each of at least one characteristic ion species of each respective compound. According to some embodiments, the calculating of the corrected intensity of at least a portion of the plurality of mass spectral measurements of a characteristic ion species may be performed on a portion of the plurality of mass spectral measurements of the characteristic ion species for which a measured intensity is greater than twenty percent of a maximum intensity measured during the acquiring of the plurality of mass spectral measurements of the characteristic ion species.

According to various embodiments in accordance with the present teachings, the acquiring of the plurality of mass spectral measurements of each of the at least one characteristic ion species may be performed during two or more injections of respective samples of the plurality of compounds into the chromatograph or other separation or fractionation apparatus, each injection corresponding to a respective one of two or more optimization experiments. Each of the two or more samples of the plurality of compounds may comprise a subset of the plurality of compounds. Each such subset may be a unique subset of the plurality of compounds and, if so, the members of each subset may be chosen, prior to the optimization experiments, such that at least a predetermined minimum number, $s_{min}$, of mass spectral measurements are acquired of each characteristic ion species of each compound of said each subset. A total required number of such optimization experiments, may be determined, prior to the optimization experiments, from a recordation, made during a prior chromatography mass spectrometry analysis (for instance, LCMS, GCMS, etc.), of a number of compounds that co-elute at each of a plurality of retention times.

According to various embodiments in accordance with the present teachings, a prior chromatography mass spectrometry analysis of the mixture of compounds may be conducted before the step of acquiring a plurality of mass spectral measurements. Such a prior survey experiment may be used to determine elution profiles of various of the compounds. Such elution profiles may be measured and recorded during the survey experiment and the recorded results may be used to generate the at least one best-fit synthetic model curve and/or to determine a required number of optimization experiments and the identities of compounds to be analyzed in each such optimization experiment. According to some alternative embodiments in accordance with the present teachings, elution profiles are not measured and recorded during a prior survey experiment but are instead measured and recorded during the step (a) of acquiring the plurality of mass spectral measurements of each of at least one characteristic ion species of each respective compound by consideration of one or more subsets of the plurality of measurements wherein, within each subset, an operational parameter is set to a non-variable control state. The elution profiles may be in the form of ion chromatograms and each such ion chromatogram may be used to generate a respective elution profile. Additionally, the survey experiment may be used to determine or recognize a mass-to-charge (m/z) ratio of each characteristic ion species. Some or all of the determined or recognized characteristic ion species may be ion species generated in an ion source during the survey experiment. Some or all of the determined or recognized characteristic ion species may be fragment ion species generated by isolation and fragmentation of certain of the ion species generated in the ion source during the survey experiment.

BRIEF DESCRIPTION OF THE DRAWINGS

The above noted and various other aspects of the present invention will become apparent from the following description which is given by way of example only and with reference to the accompanying drawings, not drawn to scale, in which:

FIG. 4A is a plot, versus applied collision energy, of normalized measured intensity of several species of fragment ions generated by fragmentation of a precursor ion species at m/z=287.1 during liquid chromatographic separation of a mixture of pesticides, where the fragment ions were repeatedly generated during chromatographic elution of the parent compound corresponding to the precursor ion;

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended figures taken in conjunction with the following description.

Figure 1A:
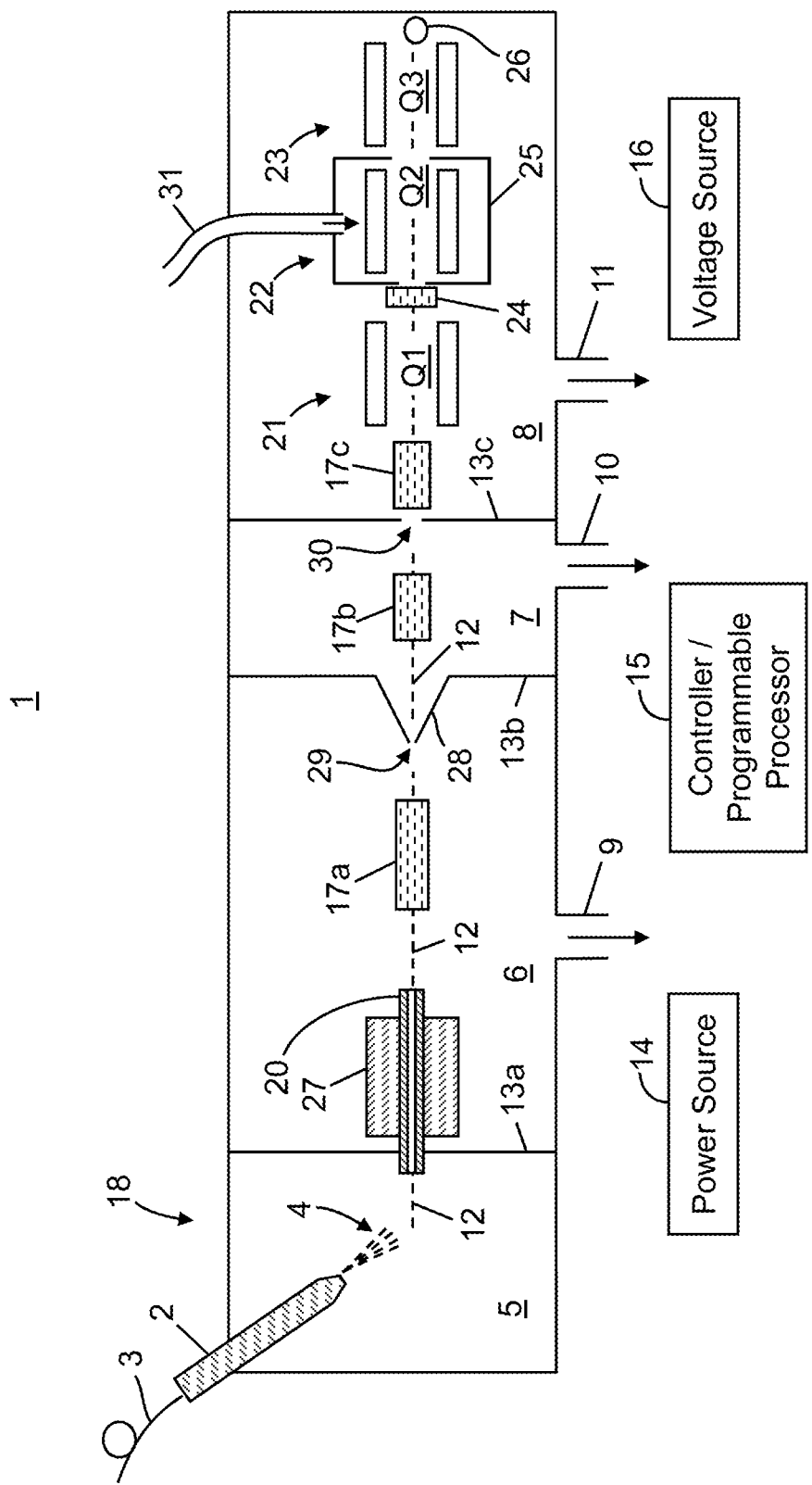
FIG. 1A is a schematic depiction of a first mass spectrometer system that may be employed in conjunction with the present teachings.

FIG. 1A is a schematic illustration of an example of a general conventional mass spectrometer system 1 capable of providing tandem mass spectrometry in accordance with the methods disclosed herein. As illustrated, the mass spectrometer system 1 comprises an ion source 18 which, in the present example, is an electrospray ionization source (ESI) having a needle 2 housed in an ionization chamber 5. More generally, the ion source may be any known type of source such as a Matrix-Assisted Laser Desorption Ionization (MALDI) ion source, a Chemical Ionization (CI) ion source, an Electron Ionization (EI) ion source, etc. In the exemplary illustration of FIG. 1A, the ESI needle 2 is connected so as to receive a liquid comprising analyte compounds from a liquid chromatograph (not shown) through fluid tubing line 3. If another form of chromatograph, such as a gas chromatograph, is employed, then a different type of ion source, for example, an EI source, may be required. The electrospray ion source 18 forms charged particles 4 (either free ions or charged liquid droplets that may be desolvated so as to release ions) representative of the sample. The emitted droplets or ions are entrained in a background or sheath gas that serves to desolvate the droplets as well as to carry the charged particles into a first intermediate-pressure chamber 6 which is maintained at a lower pressure than the pressure of the ionization chamber 5 but at a higher pressure than the downstream chambers of the mass spectrometer system. The ion source 18 may be provided as a "heated electrospray" (H-ESI) ion source comprising a heater that heats the sheath gas that surrounds the droplets so as to provide more efficient desolvation. The charged particles may be transported through an ion transfer tube 20 that passes through a first partition element or wall 13a into the first intermediate-pressure chamber 6. The ion transfer tube 20 may be physically coupled to a heating element or block 27 that provides heat to the gas and entrained particles in the ion transfer tube so as to aid in desolvation of charged droplets so as to thereby release free ions.

The ions are subsequently transported through the intermediate-pressure chambers 6 and 7 of successively lower pressure in the direction of ion travel. A second plate or partition element or wall 13b separates the first intermediate-pressure chamber 6 from the second intermediate-pressure chamber 7. Likewise, a third plate or partition element or wall 13c separates the second intermediate-pressure region 7 from the high-vacuum chamber 8 that houses a mass analyzer 23 component of the mass spectrometer system. A first ion optical assembly or set of elements 17a provides an electric field that guides and focuses the ion stream leaving ion transfer tube 20 along ion path 12 and through an aperture 29 in the second partition element or wall 13b that may be an aperture of a skimmer 28. A second ion optical assembly 17b may be provided so as to transfer or guide ions to an aperture 30 in the third plate or partition element or wall 13c and, similarly, another ion optical assembly 17c may be provided in the high vacuum chamber 8 containing a mass analyzer 23. The ion optical assemblies or lenses 17a-17c may comprise transfer elements, such as, for instance multipole ion guides, so as to direct the ions through apertures 29, 30 and into the mass analyzer 23. The mass analyzer 23 comprises one or more detectors 26 whose output can be displayed as a mass spectrum. Vacuum ports 9, 10 and 11 which are fluidically coupled to one or more vacuum pumps (not shown) may be used for evacuation of the various vacuum chambers.

The mass spectrometer system 1 is in electronic communication with a controller or other programmable processor (or processors) 15 which includes hardware and/or software logic for performing data analysis and control functions. Such controller or programmable processor (or processors) is herein simply referred to as a "controller" and may be implemented in any suitable form, such as one or a combination of specialized or general purpose processors, field-programmable gate arrays, and application-specific circuitry. In operation, the controller effects desired functions of the mass spectrometer system (e.g., analytical scans, isolation, and dissociation) by adjusting voltages (for instance, RF, DC and AC voltages) applied to the various electrodes of ion optical assemblies 17a-17c and quadrupoles or mass analyzers 21, 22 and 23. The controller 15 may also receive and process signals from the detector or detectors 26. The controller 15 may be additionally configured to store and run operational methods in which output actions are selected and executed in real time based on the application of input criteria to the acquired mass spectral data. The operational methods, as well as the other control and data analysis functions, will typically be encoded in software or firmware instructions executed by the controller 15. A power source 14 supplies an RF voltage to electrodes of the devices and a voltage source 16 is configured to supply DC voltages to predetermined devices.

As illustrated in FIG. 1A, the mass spectrometer system 1 is a triple-quadrupole system comprising a first quadrupole device 21, a second quadrupole device 22 and a third quadrupole device 23, the last of which is a mass analyzer comprising one or more ion detectors 26. The first, second and third quadrupole devices may be denoted as (using common terminology) Q1, Q2 and Q3, respectively. A lens stack 24 disposed at the ion entrance to the second quadrupole device 22 may be used to provide a first voltage point along the ions' path. The lens stack 24 may be used in conjunction with ion optical elements along the path after lens stack 24 to impart additional kinetic energy to the ions. The additional kinetic energy may utilized in order to effect collisions between ions and neutral gas molecules within the second quadrupole device 22.

Various modes of operation of the triple quadrupole system 1 are known. In one common mode of operation, the first quadrupole device 21 may be operated as a mass filter such that only ions having a certain restricted range of mass-to-charge ratios are transmitted therethrough while ions having other mass-to-charge ratios are ejected away from the ion path 12. In many modes of operation, the second quadrupole device 22 is employed as a fragmentation device or collision cell which causes collision induced fragmentation of selected precursor ions through interaction with molecules of an inert collision gas introduced through tube 31 into a collision cell chamber 25. In such operational modes, the second quadrupole 22 may be operated as an RF-only device which functions as an ion transmission device for a broad range of mass-to-charge ratios. The precursor and/or fragment ions are transmitted from the second quadrupole device 22 to the third quadrupole device (mass analyzer) 23 for mass analysis of the various ions.

Figure 1B:
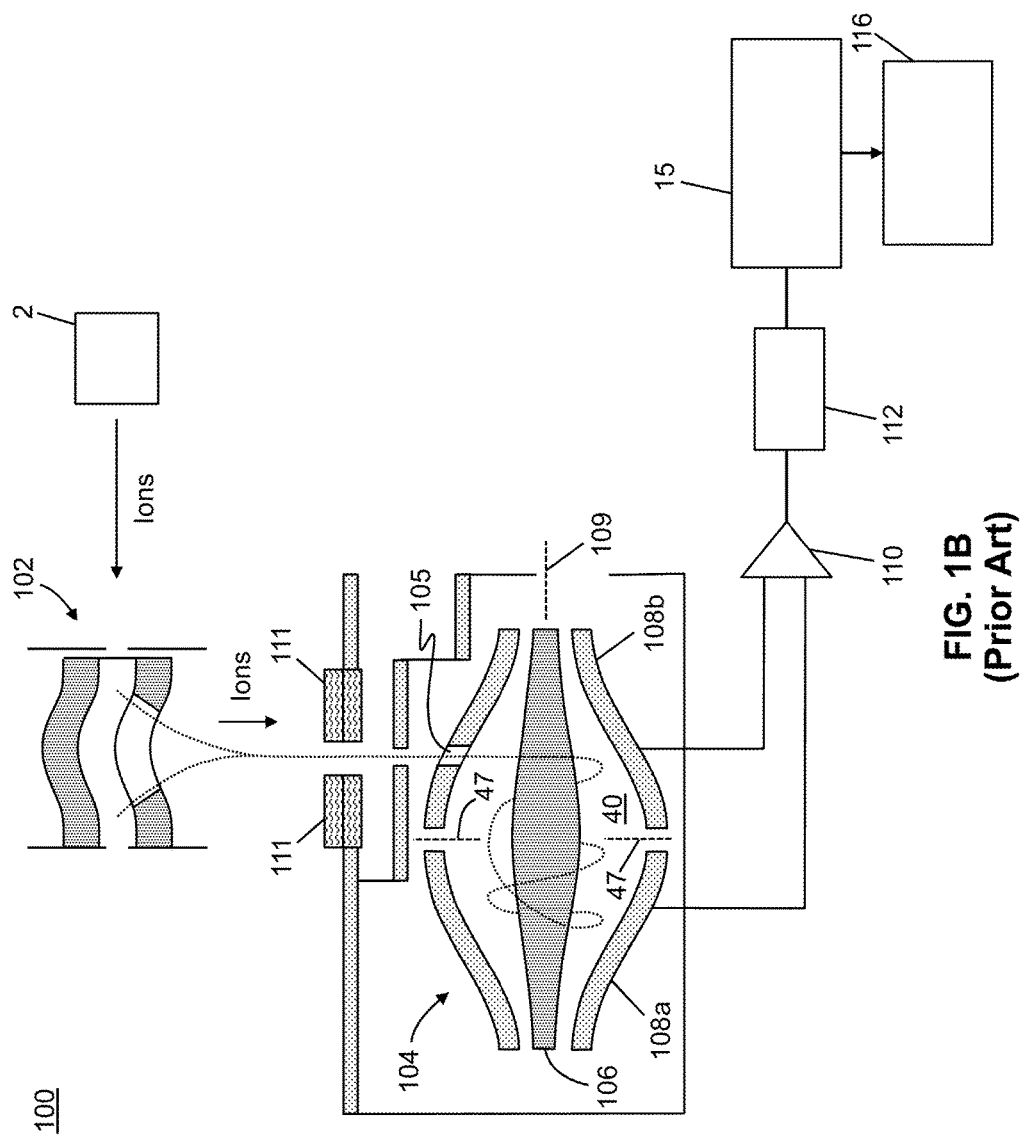
FIG. 1B is a schematic depiction of a portion of a second mass spectrometer system that may be employed in conjunction with the present teachings, the system including an electrostatic trap mass analyzer.

FIG. 1B is a schematic depiction of a portion of a second mass spectrometer system 100 that may be employed in conjunction with the present teachings. Specifically, the mass spectrometer system 100 includes an ORBITRAP™ electrostatic orbital trapping mass analyzer 104 which is schematically illustrated in longitudinal section view. The mass spectrometer system 100 further includes an ion injection device 102 for delivering ions to the mass analyzer 104. As illustrated, the ion injection device comprises a curved multipolar trap (known as a "C-trap") that may receive and trap ions from ion source 2 prior to injection into the mass analyzer 104. Ions having various m/z values which are trapped within the C-trap are generally injected from the C-trap into the electrostatic orbital trapping mass analyzer 104 in a short packet through an ion inlet aperture 105. The transfer of packets of ions is controlled by the application of electrical potential differences between the C-trap 102 and a set of injection electrodes 111 disposed between the C-trap 102 and the mass analyzer 100. Additional not-illustrated ion processing components (e.g., ion guiding components, mass filtering components, linear ion trapping components, ion fragmentation components, etc.) such as are shown in FIG. 1A may optionally be included in the mass spectrometer system 100. These and various other conventional components of the mass spectrometer system 100, such as a vacuum pumping system, power supplies etc., are not-illustrated in FIG. 1B.

The electrostatic orbital trapping mass analyzer 104 comprises a central spindle shaped electrode 106 and a surrounding outer electrode which is separated into two halves 108a and 108b. The annular space 40 between the inner spindle electrode 106 and the outer electrode halves 108a and 108b is the volume in which the ions oscillate and comprises a measurement chamber in that the motion of ions within this volume provides the measured signal that is used to the ions m/z ratios and relative abundances. The internal and external electrodes (electrodes 106 and 108a, 108b) are specifically shaped such that, when supplied with a voltage, will produce, within the measurement chamber 40, a so-called "quadro-logarithmic field" (sometimes also referred to as a "hyper-logarithmic field") potential which is radially symmetric about a longitudinal axis 109 of the measurement chamber 40 and which has a potential well at and mirror symmetry across an equatorial plane 47 of the chamber.

The motions of ions trapped within the ORBITRAP™ mass analyzer 104 are associated with three characteristic oscillation frequencies: a frequency of rotation around the central electrode 106, a frequency of radial oscillations and a frequency of axial oscillations along the z-axis. The axial oscillation frequencies are the only ones used for mass-to-charge ratio determinations. The outer electrode is formed in two parts 108a, 108b as described above for this purpose. In operation, ions of each mass-to-charge value (m/z) oscillate with a respective frequency, $\omega(m/z)$, of harmonic motion in the axial direction. One or both of the outer electrodes 108a and 108b serve as detection electrodes. The oscillation of the ions in the mass analyzer causes an image charge to be induced in the electrodes 108a and 108b. The resulting image current in the connected circuitry is picked-up as a signal and amplified by an amplifier 110 connected to the two outer electrodes 108a and 108b which is then digitized by a digitizer 112. The resulting digitized signal (i.e. the transient) is then received by controller 15 and stored in memory 116. A mass spectrum may be derived by application of a Fourier transform or other similar spectral analysis technique to the transient signal.

Figure 1C:
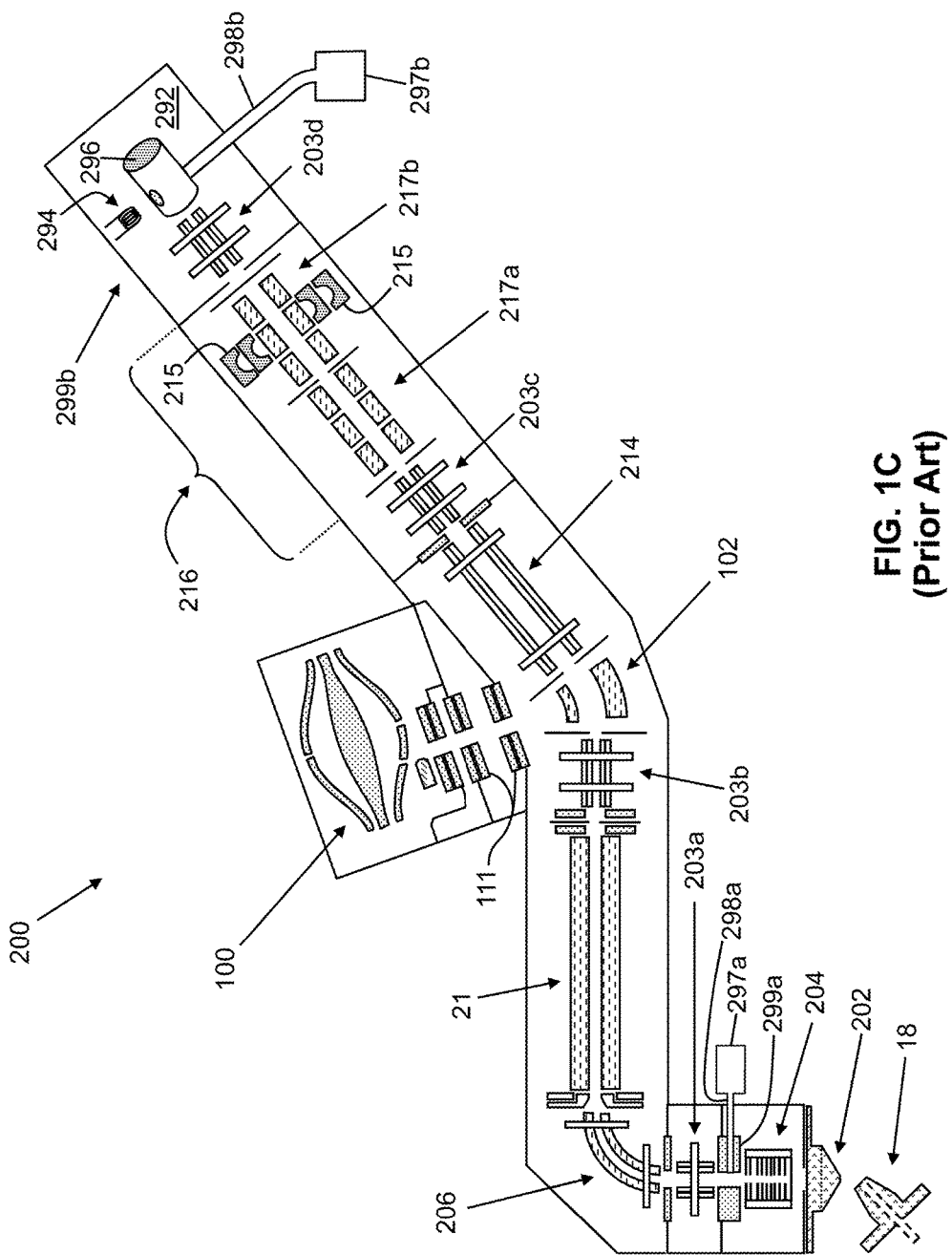
FIG. 1C is a schematic depiction of a third mass spectrometer system that may be employed in conjunction with the present teachings, the mass spectrometer comprising a hybrid system comprising a quadrupole mass filter, a dual-pressure quadrupole ion trap mass analyzer and an electrostatic trap mass analyzer.
Figure 2A:
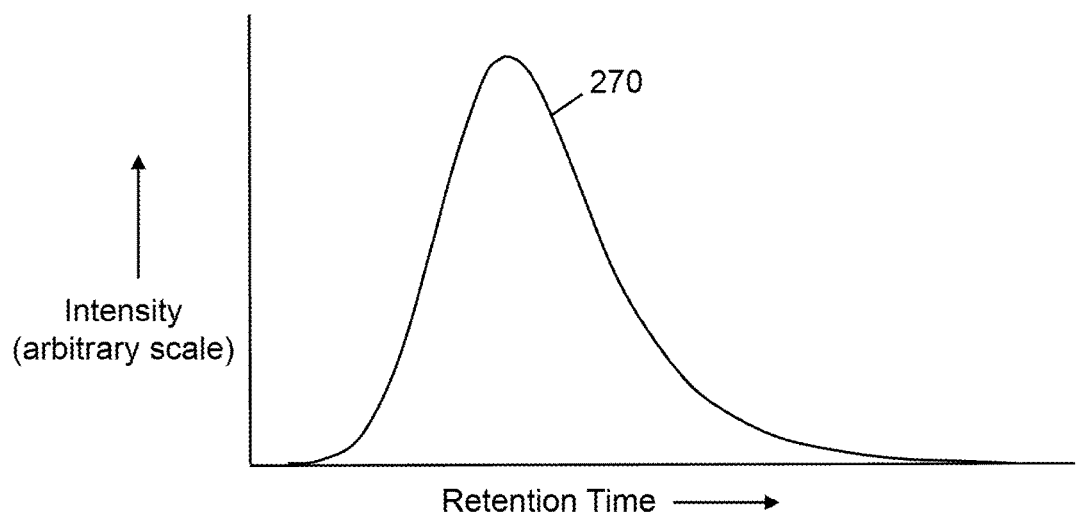
FIG. 2A is a schematic example of an elution profile of an analyte as may be detected by a mass spectrometer upon emission of the analyte from a chromatographic column.

FIG. 1C is a schematic depiction of a third exemplary mass spectrometer 200 which may be employed in conjunction with the present teachings. The mass spectrometer illustrated in FIG. 2 is a hybrid mass spectrometer, comprising more than one type of mass analyzer. Specifically, the mass spectrometer 200 includes both an ion trap mass analyzer 216 as well as an Orbitrap™ electrostatic trap mass analyzer 100. Such a hybrid mass spectrometer system can be advantageously employed to improve duty cycles by using two or more analyzers simultaneously. In operation of the mass spectrometer system 200, an ion source 18 (which may be an electrospray ion source as already described) provides ions of a sample to be analyzed to an aperture of a skimmer 202, at which the ions enter into a first vacuum chamber. After entry, the ions are captured and focused into a tight beam by a stacked-ring ion guide 204. A first ion optical transfer component 203a transfers the beam into downstream high-vacuum regions of the mass spectrometer. Most remaining neutral molecules and undesirable high-velocity ion clusters, such as solvated ions, are separated from the ion beam by a curved beam guide 206. The neutral molecules and ion clusters follow a straight-line path whereas the ions of interest are caused to bend around a ninety-degree turn by the curvature of the electrostatic pseudo-potential well that parallels the curvature of the quadrupole rods, thereby separating ions from neutrals. Additionally, an internal drag field may be applied to urge ions through the quadrupole.

A quadrupole mass filter 21 of the mass spectrometer 200 is used in its conventional sense as a tunable mass filter so as to pass ions only within a selected narrow m/z range. A subsequent ion optical transfer component 203b delivers the filtered ions to a curved quadrupole ion trap ("C-trap") component 102. The C-trap 102 is able to transfer ions along a pathway between the quadrupole mass filter 21 and the ion trap mass analyzer 216. As previously noted, the C-trap 102 also has the capability to temporarily collect and store a population of ions and then deliver the ions, as a pulse or packet, into the Orbitrap™ mass analyzer 100. The transfer of packets of ions is controlled by the application of electrical potential differences between the C-trap 102 and a set of injection electrodes 111 disposed between the C-trap 102 and the Orbitrap™ mass analyzer 100. The curvature of the C-trap is designed such that the population of ions is spatially focused so as to match the angular acceptance of an entrance aperture 105 of the mass analyzer 100.

Multipole ion guide 214 and optical transfer component 203b serve to guide ions between the C-trap 102 and the ion trap mass analyzer 216. The multipole ion guide 214 provides temporary ion storage capability such that ions produced in a first processing step of an analysis method can be later retrieved for processing in a subsequent step. The multipole ion guide 214 can also serve as a fragmentation cell. Various gate electrodes along the pathway between the C-trap 102 and the ion trap mass analyzer 216 are controllable such that ions may be transferred in either direction, depending upon the sequence of ion processing steps required in any particular analysis method.

The ion trap mass analyzer 216 is a dual-pressure linear ion trap (i.e., a two-dimensional trap) comprising a high-pressure linear trap cell 217a and a low-pressure linear trap cell 217b, the two cells being positioned adjacent to one another separated by a plate lens having a small aperture that permits ion transfer between the two cells and that presents a pumping restriction and allows different pressures to be maintained in the two traps. The environment of the high-pressure cell 217a favors ion cooling, ion fragmentation by either collision-induced dissociation or electron transfer dissociation or ion-ion reactions such as proton-transfer reactions. The environment of the low-pressure cell 217b favors analytical scanning with high resolving power and mass accuracy. The low-pressure cell includes a dual-dynode ion detector 215.

The mass spectrometer 200, as depicted in FIG. 2, illustrates two alternative reagent-ion sources for generating fragments by ion-ion chemical reactions, a first reagent-ion source 299a disposed between the stacked-ring ion guide 204 and the curved beam guide 206 and a second reagent-ion source 299b disposed at the opposite end of the instrument, adjacent to the low-pressure cell 217b of the linear ion trap mass analyzer 216. Generally, any particular system will only include one reagent ion source at most. However, two different reagent ion sources are depicted and discussed here for illustrative purposes. The reagent ion source 299a may comprise a glow discharge cell comprising a pair of electrodes (anode and cathode) that are exposed to a reagent gas conduit 298a that delivers the reagent gas from a reagent liquid (or solid) reservoir 297a having a heater that volatilizes the reagent compound. When a high voltage is applied across the electrodes, glow discharge is initiated which ionizes the reagent flowing between the electrodes. Reagent anions from the reagent ion source 299a are introduced into the ion optics path ahead of the quadrupole mass filter 21 within which they may be m/z selected. The reagent ions may then be accumulated in the multipole ion guide 214, and subsequently transferred into the high pressure cell 217b of the dual-pressure linear ion trap 216 within which they are made available for the ion-ion reaction. The reaction products may be directly transferred to the low pressure cell 217a or to the Orbitrap™ mass analyzer 100 for m/z analysis.

A possible alternative reagent ion source 299b may be located adjacent to the low pressure linear trap cell 217b where it may comprise an additional high-vacuum chamber 292 from which reagent ions may be directed into the high pressure cell 217b through an aperture in between chamber 292 and the high-pressure cell. In operation, gaseous reagent compound is supplied from a reagent liquid (or solid) reservoir 297b having a heater that volatilizes the reagent compound and is directed through a reagent gas conduit 298b that delivers the reagent gas into a partially confined ion generation volume 296. In operation, thermionic electrons supplied from an electrically heated filament 294 are directed into the ion generation volume 296 with a certain pre-determined energy by application of an electrical potential between the filament 294 and an accelerator electrode (not shown). The supplied energetic electrons cause ionization of the reagent gas so as to generate reagent ions. The reagent ions may then be guided into the high pressure cell 217b by ion optical transfer component 203a under the operation of gate electrodes (not shown).

The mass spectrometer systems illustrated in FIGS. 1A-1C are just some examples of mass spectrometer systems that may be employed in conjunction with methods in accordance with the present teachings. Many other types of mass spectrometer systems, such as those based on time-of-flight (TOF), Fourier Transform Ion Cyclotron Resonance (FT-ICR) or magnetic sector mass analyzers, may also be employed in conjunction with these methods. Each such mass spectrometer system is associated with various operational parameters that should be optimized, prior to conducting mass spectrometry experiments, in order to obtain the best analytical results.

In accordance with the present teachings, optimization of MS parameters is carried out by acquiring mass spectra of known compounds over a range of settings of one or more of the parameters and computing one or more metrics of interest from the spectra. For example, with particular regard to tandem mass spectrometry (MS/MS), the total area mass spectral signal attributable to the fragment ions can be used as a metric. Typically, an optimization assumes that the flux of a compound of interest is constant, and any change in the metric can be attributed to the change of the independent variable (or else to a source of noise). However, when a compound is injected into a mass spectrometer in a small volume in a liquid or gaseous stream, such as from a liquid chromatograph (LC), gas chromatograph (GC) or other fractionation apparatus, its concentration may vary with time. In order to correctly compute the metric of interest, the effects of this time-varying concentration must be separated from the variation attributable to the variation of the operational parameters.

Time-varying analyte concentration is typical during liquid chromatographic separation or other chromatographic separation combined with mass spectrometric detection (e.g., LCMS, GCMS, etc.). An example elution profile 270 is given in FIG. 2A. The presence of time-varying concentration profiles, such as elution profiles, can confound a conventional optimization procedure because variation in the metric may be the result of one or more of several factors, including not only the variation of the parameter to be optimized (e.g. collision energy) but also the changing compound concentration. This situation is explained simply by Eq. 1, $$m(p,t) = f(p)c(t) \qquad \text{Eq. 1}$$

where the metric of interest, $m(p,t)$, is the product of instrument and analyte compound response factors, $f(p)$, and the concentration of the compound with time, $c(t)$ and where where t represents time and the vector p is a collection of one or more adjustable instrumental or operational parameters (e.g., $p = p_1, p_2, \ldots, p_k$ where $k \geq 1$).

Fortunately, elution profiles can be modeled relatively accurately. For example, U.S. Pat. No. 7,983,852 teaches methods for modeling an elution profile, after baseline subtraction, by a model curve, $\mathcal{F}(t)$, having either a Gaussian, an exponentially modified Gaussian or a Gamma line shape or by a model curve, comprising a pair of Gaussian curves. Gaussian functions are generally used to model symmetric peaks, and exponentially-modified Gaussians or Gamma functions are used to model skewed peaks. To remove the influence of the compound concentration, one can simply multiply by the inverse of the model function, i.e.

$$f(p) = m(p,t)\mathcal{F}^{-1}(t) = f(p)c(t)\mathcal{F}^{-1}(t) = f(p)\mathcal{F}(t)\mathcal{F}^{-1}(t) \qquad \text{Eq. 2}$$

Figure 2B:
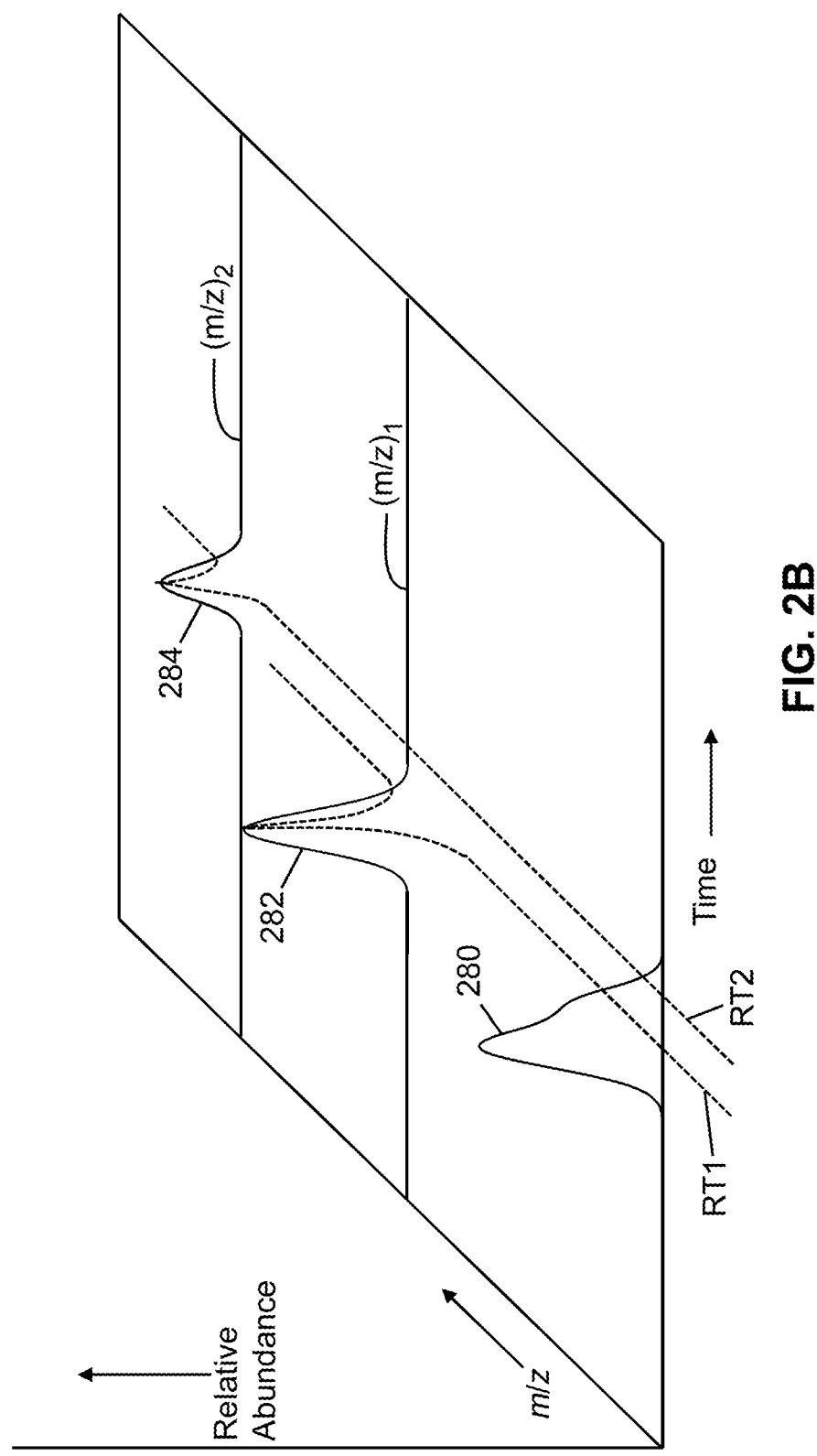
FIG. 2B is a schematic depiction of the elution of partially-coeluting analytes, where the elution of each analyte is separately detected by measurement of a respective extracted ion chromatogram.

FIG. 2B schematically depicts a common situation in which elution profiles of different compounds overlap (at least partially) in time. For example, profiles 282 and 284 represent the elution profiles, in time, of a first compound and a second compound, respectively, where the first compound and second compound are detected by detection of representative ions having mass-to-charge ratios $(m/z)_1$ and $(m/z)_2$, respectively. Elution profile 282 has a peak value at retention time RT1 and elution profile 284 has a peak value at a slightly different retention time RT2. In this example, the elution profiles partially overlap because the width of each profile is on the order of or greater than the time difference between the two peak retention times. Depending on which of the compounds is being investigated during a particular optimization experiment, either one of elution profile 282 or elution profile 284 may correspond to the correct model curve, $\mathcal{F}(t)$, to employ in Eq. 2 above. Separate model curves, $\mathcal{F}_1(t)$ and $\mathcal{F}_2(t)$, may be derived by separately mathematically fitting the profiles 282, 284 by any suitable technique, such as the techniques described in U.S. Pat. No. 7,983,852.

Generally, the partial overlap, in time, of the two elution profiles 282, 284 is not problematical because a typical optimization experiment will be designed such that the mass-to-charge values, $(m/z)_1$ and $(m/z)_2$, are well resolved by a mass spectrometer apparatus. Thus, both such profiles may be determined independently of one another by measuring ion intensities at each of $(m/z)_1$ and $(m/z)_2$, at each of several time values, during the course of the co-elution. Each such detected ion profile is then a respective selected-ion chromatogram (or, simply, an ion chromatogram). Occasionally, the separate mass-to-charge values, $(m/z)_1$ and $(m/z)_2$, may not be resolved and, in this case, a composite ion chromatogram of the form of profile 280 may be recorded. Such a composite ion chromatogram of the form of profile 280 may be recorded, for example, if a separate detector, other than a mass spectrometer, that measures total ion content without mass-to-charge discrimination, is used to obtain the profile. In such instances, the separate model curves, $\mathcal{F}_1(t)$ and $\mathcal{F}_2(t)$, may be derived by mathematical deconvolution techniques, such as the techniques described in U.S. Pat. No. 7,983,852.

To demonstrate the practicality of the experimental approach implied by Eq. 2, an experiment was performed in which a mixture of pesticides was separated into its component compound fractions by liquid chromatography and in which, during the separate elution peak of each compound of interest, a series of tandem mass spectra were acquired using either randomized collision energies, or zero collision energy and a randomized source RF amplitude. During the acquisition of each such series of tandem mass spectra, one or more precursor ions of the corresponding compound of interest were separately isolated and fragmented repeatedly during the elution of the compound. The signal intensities relating to each fragment ion were recorded for each such fragment-ion mass spectrum. Also, ion chromatograms of the selected precursor ions were obtained during the elution of each compound. Each such ion chromatogram was constructed from a subset of the data for which the collision energy was set at a non-variable control value. The data points for which the collision energy was set at the non-variable control value were interspersed among data points for which the collision energy was randomly varied. By constructing each ion chromatogram only from data points pertaining to the non-varying control value of the collision energy, the intensity variation attributable to the elution profile of the parent compound of the precursor ions may be separated from the variation attributable to the randomized variation of collision energy. The resulting ion chromatogram profiles were fit using the methods taught in U.S. Pat. No. 7,983,852 so as to derive a set of appropriate model curves, $\mathcal{F}_i(t)$, where the index, i, relates to enumeration of the various characteristic precursor ion species, each characteristic precursor ion species corresponding to one of the compounds. The goal of this experiment was to demonstrate the feasibility of optimizing these two independent parameters (collision energy and source RF amplitude) for each compound of interest during the course of a single LC injection. FIGS. 3A, 3B, 4A, 4B and 5 show selected raw and processed data from this experiment.

Figure 3A:
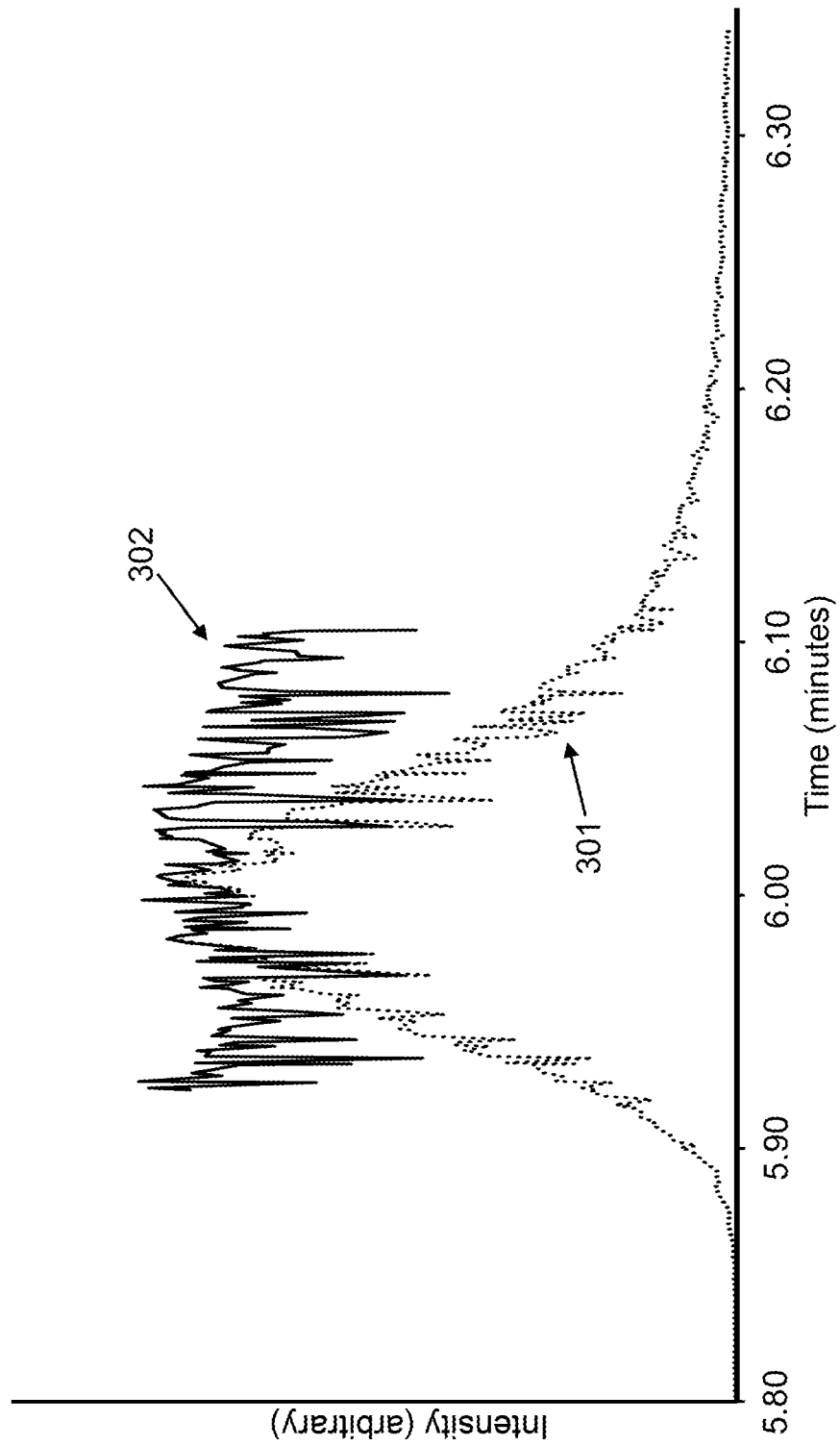
FIG. 3A is a plot, versus retention time, of the measured intensity of fragment ions generated by fragmentation of a precursor ion species at m/z=287.1 during liquid chromatographic separation of a mixture of pesticides, showing separate plots for raw data and corrected data, where the corrected data is derived by scaling the raw data by a time-varying scaling factor derived from the precursor ion elution profile.

FIG. 3A depicts the total signal intensity, versus time, of fragment ions generated by fragmentation of a precursor ion at m/z=287.1 Da during one identified elution peak and with repeated fragmentation using random collision energies. Unscaled data are shown by dotted line 301, whereas corrected data that have been scaled by using an appropriate scaling function, $\mathcal{F}_i^{-1}(t)$, are shown by solid line 302. Note that the scaling is not applied over the entirety of the chromatographic elution peak but, instead, is applied only over the region of the peak for which the raw intensity is ≥20% of the maximum fitted intensity. Note that, in this example, the corrected data is only calculated between the time points $t_1$=5.92333 minutes and $t_2$=6.10474 minutes. For this reason, the curve 302 representing the corrected data only spans the portion of the time range between these limits. In general, this selective scaling is applied so as to only consider the time region where the model best fits the raw data, which in general is at ≥20% of the maximum fitted intensity.

Figure 3B:
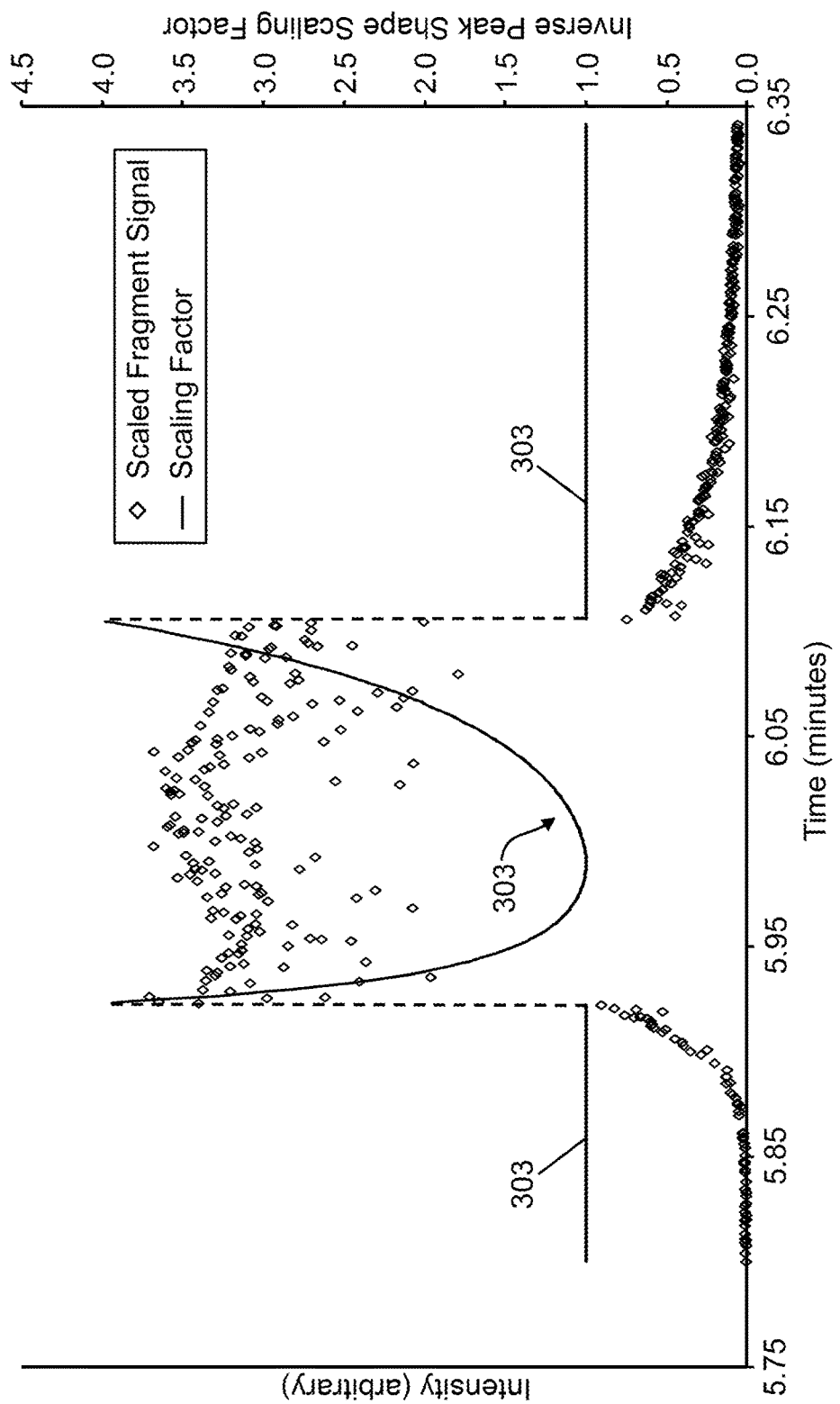
FIG. 3B is a plot, versus retention time, of the measured intensity of fragment ions generated by fragmentation of a precursor ion species at m/z=287.1 during liquid chromatographic separation of a mixture of pesticides, also showing a plot of the scaling factor employed to generate corrected data.

FIG. 3B is a plot of the same corrected data as depicted by line 302 of FIG. 3A instead plotted as individual points. The solid-line curve 303 in FIG. 3B is the applied scaling factor, which is calculated from the fitted elution profile only between the time points $t_1$=5.92333 minutes and $t_2$=6.10474 minutes (represented by vertical dashed lines in FIG. 3B) and is set equal to unity elsewhere. By comparison of line 302 with line 301 (FIG. 3A), it is apparent that, although the random collision energy does have a visually discernible effect on the total fragment-ion signal intensity (the metric being employed in this instance), this effect is overwhelmed by the larger elution profile effect (FIG. 3A). On the other hand, when the data are scaled by the inverse of the model fit function for the elution profile, the effect of the elution is removed, and the remaining variation in the metric is due to the randomized collision energies (FIG. 3B). Most of the apparent scatter in the corrected data points between vertical dashed lines in FIG. 3B is not due to uncontrolled "noise" but is instead the result of the application of the randomized collision energy, which can be analyzed as discussed below.

Figure 4B:
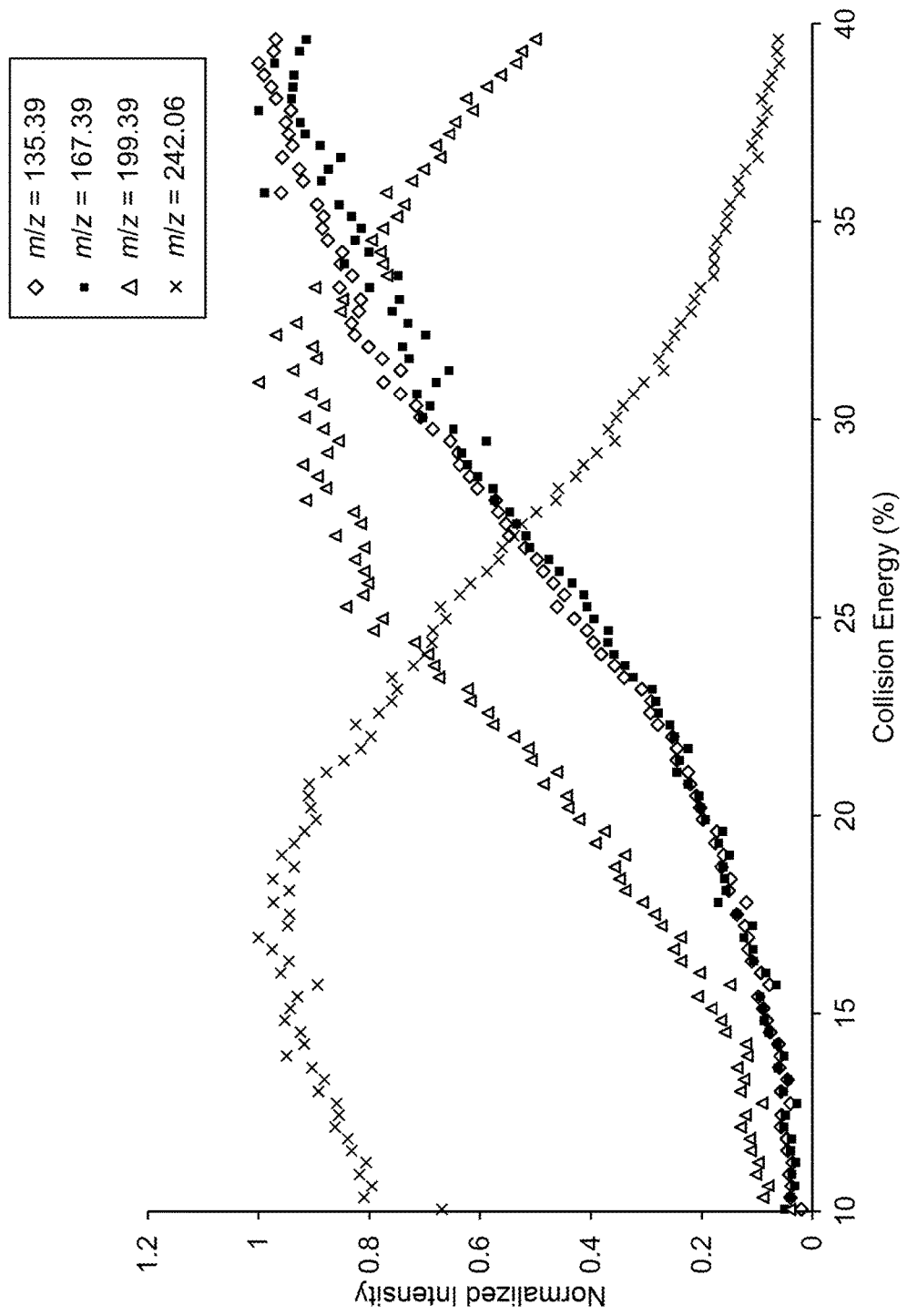
FIG. 4B is a plot, versus applied collision energy, of normalized corrected intensity of the several species of fragment ions of FIG. 4A, after application of a time-varying scaling factor derived from the precursor ion elution profile.

FIG. 4A is a plot of uncorrected signal intensity of four different fragment ions formed by fragmentation of the precursor ion at m/z=287.1 Da, plotted as a function of collision energy. The different fragment ions (at m/z=135.39 Da, m/z=167.39 Da, m/z=199.39 Da and m/z=242.06 Da, respectively identified by different symbols) exhibit a significant amount of scatter in them due to the elution profile, thereby rendering it difficult to identify a best collision energy value for each ion. However, the scaled data (shown in FIG. 4B) are much cleaner. The scaled data indicate that, for certain experiments, different collision energy values may be employed for different ions so as to provide the most reliable results for each and every ion. Alternatively, the scaled data may be used to choose, for certain other experiments, a certain single best-compromise collision energy that might be chosen to maximize some metric, such as the total abundance of a fragment or fragments, or the total number of fragments produced, or some combination of these data. For example, in the present example (FIG. 4B), a collision energy value of twenty-seven percent may be regarded as a best-compromise value, since it gives good abundance of fragments of all investigated precursor ions.

Figure 5:
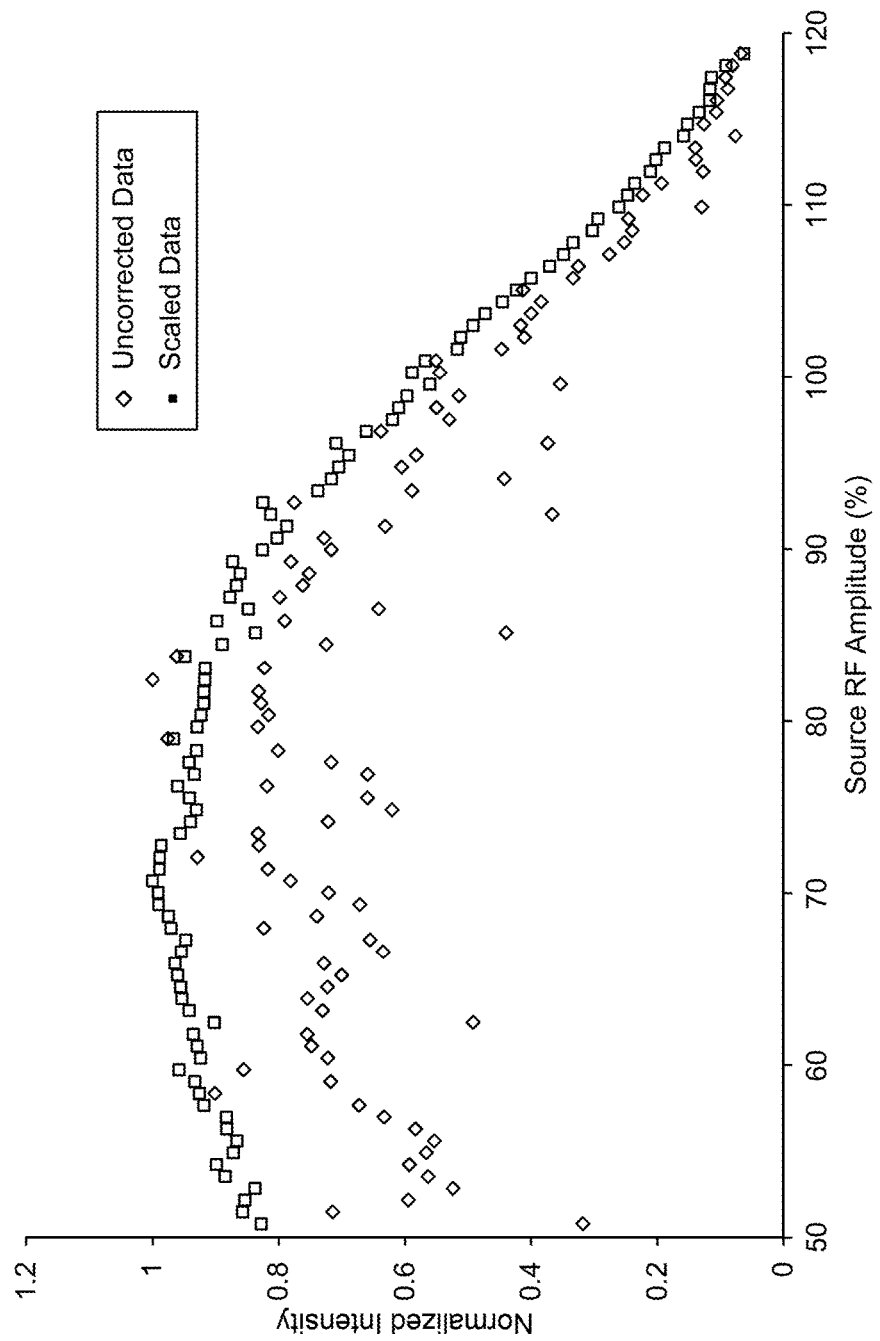
FIG. 5 is a plot, versus applied source RF voltage, of the measured intensity of precursor ions, the ions generated during liquid chromatographic separation of a mixture of pesticides at m/z=287.1, during programmed variation of the applied source RF voltage during liquid chromatographic separation of a mixture of pesticides, showing separate plots for raw data and corrected data, where the corrected data is derived by scaling the raw data by a time-varying scaling factor derived from the precursor ion elution profile.

The above-illustrated procedure for removing the influence, on an operational metric, of a compound's concentration variation during the course of chromatographic elution is here termed the "elution profile compensation technique". The elution profile compensation technique is attractive because it lends itself to the optimization of any parameter. For example, in the same LC injection, an optimal value of source RF amplitude was determined by inserting mass spectral events in which there is no application of collision energy, but randomized source RF amplitude. The same elution profile correction was applied to the data relating to the variation of source RF amplitude. FIG. 5 is a plot of both uncorrected data and scaled data, as applied above, relating to the repeated measurements of the intensity of the aforementioned precursor ion (at m/z=287.1 Da) without fragmentation and with randomized values of the RF source voltage. Thus, from the set of measurements on a single elution peak, the optimal values of at least five operational parameters—collision energies for detection of four different fragment ions and source RF voltage for particular precursor ion—may be discerned. Any optimization will have a much higher chance of success operating on the scaled data, where the effect of collision energy on the metric stands out. As the number of data points collected is decreased (narrower LC peaks), it becomes even more important to eliminate the elution profile effect from the data.

An alternative method for eliminating the effect of the compositional variation caused be an elution profile may be recognized in certain situations in which a metric can be computed from ratios of mass spectral signals across multiple scans or from differences of mass spectral signals between multiple scans. For example, in the case of optimizing collision energy, it is well known that the efficiency of fragmentation can be determined by the ratio of data from two MS/MS spectra. For example, a ratio of the signal intensity attributable to a certain fragment ion may be determined from two such MS/MS spectra, where different collision energies are employed in the two fragmentation steps. As another example, the ratio of the total mass spectral signal attributable to fragment ions to the signal attributable to precursor ions may be determined from two successive mass spectra—a first MS/MS spectrum employing an non-zero collision energy and a second precursor-ion scan employing no collision energy. If these two mass spectral measurements are alternated very quickly, the change in the metric due to concentration changes will be small compared to the variation in the metric attributable to the changed operational parameters. This alternative method is here termed the "ratio technique". This ratio method is much less general, however, and for example cannot be applied to optimizing the source RF amplitude.

The procedures described above—that is, the elution profile compensation technique and, as an alternative, the ratio technique—may each be useful as a standalone procedure, in certain non-complex circumstances, such as circumstances corresponding to a relatively small number of parameters to be optimized or a small number of compounds of interest or well-separated compound retention times or some combination thereof. Such circumstances correspond to a near-perfect situation in which only one LC injection would be needed to optimize all the parameters. More generally, each of the elution profile compensation technique and the ratio technique may be regarded as a possible component step of a more-complex multi-step optimization process.

When LC features are reasonably separated from one other, a multi-step optimization process may also include one or more steps based on so-called data dependent acquisition (DDA). In a general sense, DDA methods may be characterized as having one or more input criteria, and one or more output actions. The input criteria employed for conventional data-dependent methods are generally based on parameters such as intensity, intensity pattern, mass window, mass difference (neutral loss), mass-to-charge (m/z) inclusion and exclusion lists, and product ion mass. The input criteria are employed to select one or more ion species that satisfy the criteria. The selected ion species are then subjected to an output action (examples of which include performing MS/MS or MSn analysis and/or high-resolution scanning on the selected ion species). In one instance of a typical data-dependent step, a group of ions are mass analyzed, and ion species having mass spectral intensities exceeding a specified threshold are subsequently selected, possibly sequentially, as precursor ions for MS/MS analysis, which can include the individual operations of isolation, dissociation of selected precursor ions, and mass analysis of the resulting product ions.

With regard to the presently-considered parameter optimization methods, a conventional application of DDA methods may include a first survey experiment in which, over the course of elution of various chromatographic fractions, mass spectra are obtained so as to identify the retention times of any eluting compounds followed by a second experiment that includes a series of DDA steps (including acquisition of MS/MS spectra) during which experimental parameters are randomized, stepped or alternated during the elution of each compound. In practice, such a procedure tends to be fairly complex and not robust, since there are many DDA settings that must be set correctly for it to work. One important problem with such a method is that, even when using targeted mass lists for the compounds of interest, the DDA steps may be triggered by false positive identifications. The response to such false triggers tends to use up the instrumental duty cycle without acquiring enough data for optimization.

Figure 6A:
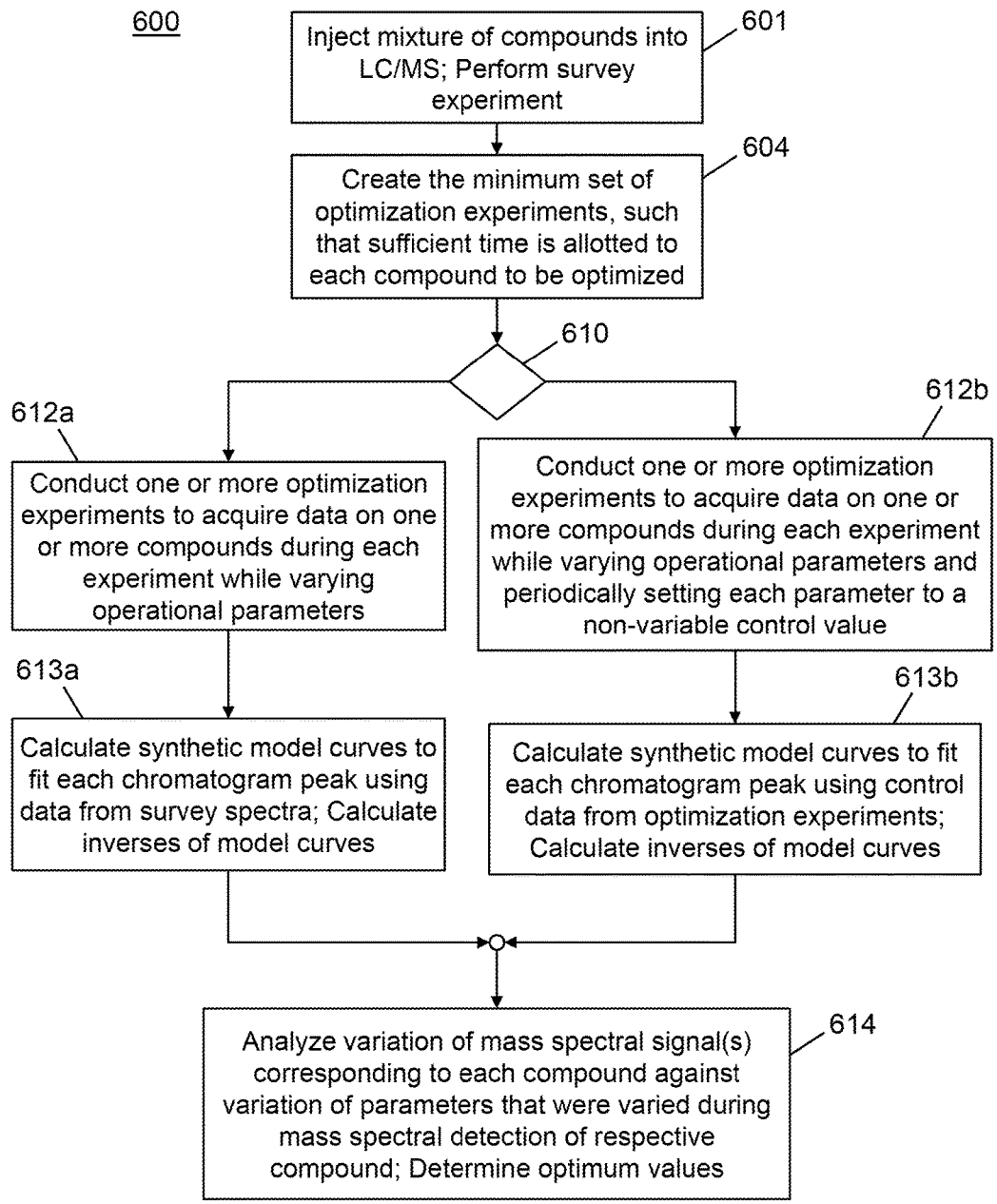
FIG. 6A is a flow diagram depicting an exemplary method in accordance with the present teachings for simultaneous optimization of multiple mass spectral operating parameters.
Figure 6B:
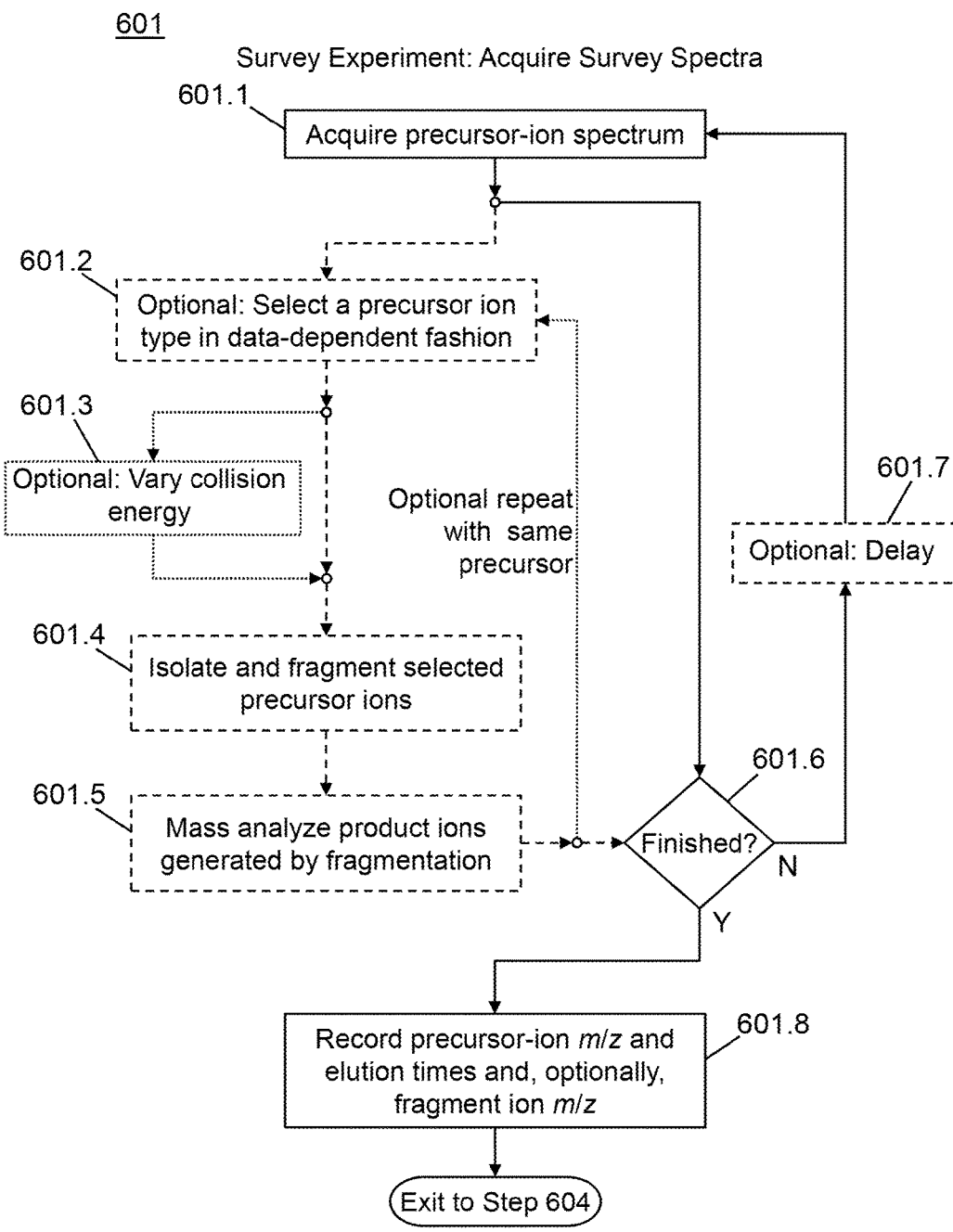
FIG. 6B is a flow diagram depicting an exemplary method in accordance with the present teachings for acquiring a survey mass spectra for gathering information for optimization of multiple mass spectral operating parameters.

In accordance with the present teachings, a more feasible, multi-step optimization method proceeds with the steps as described below and as also outlined in the method 600 shown in FIG. 6A. In the first step, Step 601, an initial injection of a portion of a sample containing a mixture of the compounds of interest is made onto an LC column of an LCMS system in the usual fashion such that the various chemical components are separated (or at least partially separated) into respective fractions. The fractions are delivered, in sequence to a mass spectrometer that receives the LC eluate and a survey experiment comprising a series of survey mass spectra of the eluate components are obtained. Using the mass spectral data, the elution times and characteristic mass-to-charge ratios corresponding to each compound of interest are determined. The mass spectra may consist only of survey mass spectra or, alternatively, one or more DDA steps (with non-optimized parameters) may be included. Accordingly, Step 601 may comprise various sub-steps, denoted as Sub-steps 601.1-601.8, some of which are optional, as further illustrated in FIG. 6B. In FIG. 6B, essential steps are indicated in solid lines and optional steps and pathways are indicated in dashed or dotted lines.

Sub-Step 601.1 (FIG. 6B) is the acquisition of a single survey mass spectrum of a portion of a fraction of a received eluate. The survey scan generally detects ions that are generated in an ion source 18 (FIGS. 1A, 1C) of a mass spectrometer system which, for convenience, are here and in Sub-Step 601.1 referred to as "precursor" ions, regardless of whether a subsequent fragmentation step is to be performed. The survey scans should repeat at an interval that is short enough to characterize the LC peaks. A general rule of thumb is that there should be at least approximately 10-15 mass spectral acquisitions across each LC peak, although the total number or frequency of mass spectral determinations (i.e., the number of times that Step 601.1 is executed or the frequency of its execution) may be determined by some other rule or calculation, as discussed further below, or may be pre-determined. Therefore, after a survey mass spectrum has been acquired (Sub-Step 601.1) and any associated optional steps have been executed (Sub-Steps 601.2-601.5, discussed in greater detail below) and if more survey mass spectra are to be acquired ("N" branch of decision Sub-Step 601.6), an optional time delay (Sub-Step 601.7) may be implemented.

Optionally, data-dependent fragmentation may be performed during the acquisition of spectra in Step 601 in an attempt to obtain additional qualitative information on the identity of the compound in each LC peak. In such instances, optional Sub-Step 601.2 is executed, in which a precursor ion type (that is, ions within a particular m/z ratio range) is selected for subsequent fragmentation. For example, the precursor ion type may be selected based on its signal intensity in the precursor ion mass spectrum obtained in the previous step. The selected ions are then isolated and fragmented so as to generate product ions in Sub-Step 601.4. The fragmentation could either use an energy that is likely to provide at least some information for most compounds of interest, or it could be varied (optional Sub-Step 601.3) by incrementing or decrementing the collision energy value relative to a previously-employed value according to a stepped collision energy program consisting of multiple fragmentation steps at various collision energies in one experiment. Alternatively, a method like resonance CID can be used for the dependent scans, for which the fragmentation of most compounds of interest is good using calibrated collision energies, but which for the actual assay may not produce all the diagnostic fragments required, or else may be prohibitively slow. In Sub-Step 601.5, the resulting product ions are mass analyzed, after which another precursor ion type may be selected for fragmentation (an optional repeat back to Sub-Step 601.2).

After acquisition of each survey precursor-ion mass spectrum (Sub-Step 601.1) and any associated product-ion mass spectra (optional Sub-Steps 601.1-601.5), Sub-Step 601.6 is executed in which a determination is made whether the more survey spectra are required. This determination may be made in any one of a variety of ways, such as by comparison of an actual elapsed experiment time to a maximum experimental time, by comparison of an elapsed time since detection of an above-threshold ion intensity to a maximum wait time, by comparison of the number of compounds detected to a maximum number of compounds to be detected, etc. If no additional survey spectra are required, then execution passes to Sub-Step 601.8 in which precursor-ion elution times and m/z values and, optionally, fragment ion m/z values are recorded (if not already recorded) for use in conjunction with subsequent steps of the method 600. Execution then proceeds to Step 604 (FIG. 6A).

Once the elution time windows have been identified for each compound of interest (Sub-Step 601.8, FIG. 6B), an analysis of the windows should be performed (Step 604, FIG. 6A), to ensure that the instrument can acquire the optimization data required in one or more optimization experiments (Step 612). For example, if the LC peaks are estimated to be about 10 seconds wide, and each MS/MS data acquisition requires on the order of 25 ms, then 400 MS/MS data acquisitions may be carried out during the elution of each LC peak. Assuming that on the order of 100 mass spectral measurements are required to make a determination of the optimum parameters for use with each particular compound, then no more than four compounds should have overlapping retention time windows at any one time. A set of optimization experiments is then constructed, based on the above constraints. When the density of compounds in a single experiment is such that the elution of more than four compounds will overlap in a given time window, then an extra optimization experiment is added, and the compounds are distributed between the existing and additional experiments to minimize overlap of elution windows. The procedure continues until the maximum density of elution windows is below the threshold.

After the number of required LCMS optimization experiments has been determined in Step 604 of the method 600, execution of the method may progress along one of two alternative independent branches indicated as diverging from the branching step 610. A first branch comprises Step 612*a* and Step 613*a*; a second branch comprises Step 612*b* and Step 613*b*. The choice of which branch to follow may be made based on user preferences, time available, the nature of the sample, the nature of delivery of the sample to the mass spectrometer, the degree of required precision, etc. The optimization experiment (or experiments) are performed in either Step 612*a* or Step 612*b*. Each such optimization experiment comprises a respective injection, into the LCMS system, of a respective portion of a sample containing a mixture of the compounds of interest investigated in the survey experiment. Preferably the sample that provides the portions used for the optimization experiments is the same sample that provided the sample portion used in the survey experiment (Step 601). As in the previous survey experiment, the mixture is chromatographically separated (or partially separated, if elution peaks overlap) into respective fractions. These fractions are delivered, in sequence, to the mass spectrometer and a series of optimization mass spectra of the eluate components are obtained during each elution.

Whereas the survey spectra (Step 601) are generally obtained throughout the course of elution during a survey experiment, the mass spectra of the optimization experiments (Step 612) may be scheduled so as to only obtain data during the various retention time windows identified in Step 601. Each such retention time window brackets the predicted elution time of one or more of the compounds of interest, as determined from the survey mass spectral data obtained in Step 601. Each such elution time window may correspond to a certain subset of precursor ions to be detected during the respective time window. The precursor ions that are detected during each such time window of each optimization experiment are preferably just those precursor ions that correspond to compounds of interest, as determined in Step 601, and that have been allotted to the particular optimization experiment using the analysis of Step 604 (which is described in greater detail below).

During the elution of each compound of interest during an optimization experiment (Step 612*a* or Step 612*b*), mass spectral signals of at least one ion type that is generated in an ion source from the respective compound and that is characteristic of the respective compound is detected and the intensity of the signal is recorded. Using the terminology of this document, such ions that are generated in the ion source are referred to as "precursor ions". Each compound of interest may give rise to more than one such characteristic precursor ion type and, if so, the signal intensity of more than one characteristic precursor ion type may be detected and recorded for each of one or more compounds of interest. Preferably, each such characteristic ion species is detected at least ten times and, more preferably, at least fifteen times, during the elution of the respective compound. If more than one compound of interest elutes at a given time (i.e., if elution time windows at least partially overlap), then the signals of characteristic ion species of each co-eluting compound may be detected and measured during the period of overlapping elution. The signals of the various characteristic precursor ion types—of either one eluting compound or a plurality of co-eluting compounds—may be generated essentially simultaneously, as would be true in the case of mass spectrometer systems that include mass analyzers that detect ions by the generation transient signals. Such mass analyzers include FT-ICR mass analyzers and ORBITRAP™ orbital electrostatic trapping mass analyzers. Alternatively, the signals of the various characteristic ion species may be generated sequentially, as would be true in the case of mass spectrometer systems that include mass analyzers that detect the ions by a scanning method. Such mass analyzers include quadrupole mass filter and quadrupole ion trap mass analyzers.

As noted above, the mass spectral signal of each characteristic precursor ion type may be detected a plurality of times during the elution time window of the respective compound of interest during an optimization experiment (Step 612a or Step 612b). In accordance with the present teachings, one or more operational parameters of the mass spectrometer system may be caused to vary during the course of the plurality of such detection events of each of one or more precursor ion types. One of the varied operational parameters may be a value of an RF voltage applied to ion guiding elements at or just downstream from an ion source of the mass spectrometer. The one or more operational parameters that are varied during the plurality of signal detection events of a characteristic precursor ion type are, preferably, operational parameters that affect the signal strength of the mass spectral signal attributable to the precursor ion. In such cases, such variation causes a component of variation in the detected intensity of the signal that would otherwise be absent, in the absence of the operational parameter variation. As previously described, the variation of detected signal intensity may also include another component of variation relating to an elution profile.

Step 612b differs from Step 612a in that, during each optimization experiment, one of the values of each operational parameter is taken as a non-variable control value to which the respective operational parameter is repeatedly reset over the course of the experiment. Preferably, each operational parameter is reset to its respective control value at approximately equal time increments. Preferably, all operational parameters are set and reset to their respective control values synchronously. If the variation of the operational parameter is otherwise random, then the times at which the operational parameter assumes its non-varying control value may be interspersed with the various times at which the value of the operational parameter is set randomly. If the variation of the operational parameter is periodic, such as according to a sinusoidal, sawtooth or triangular waveform, then the control value may be a particular one of the set of values that the operational parameter assumes during each period. By periodically setting each operational parameter to its constant control value, the component of mass spectrometer signal variation relating to an elution profile may be separated from the component of the signal variation that relates to variation of the respective operational parameter.

Step 613a is executed in the first branch of the method 600 and may be executed either before or after execution of Step 612a. Step 613a comprises modeling each peak in one or more baseline-corrected chromatograms of the sample (as measured in the survey spectra obtained in Sub-Step 601) by a respective synthetic best-fit curve. Step 613b is executed in the second branch of the method 600 and is executed after the execution of Step 612b. In similarity to Step 613a, Step 613b comprises modeling each peak in one or more baseline-corrected chromatograms of the sample by a respective synthetic best-fit curve. However, in Step 613b, the data for the modeling is obtained from the optimization experiments of Step 612b and is taken from the data points at which the control parameters are set or reset to their control values. The variation of observed mass spectral intensity profiles with time, as derived from these data points, reveal the component of variation of each mass spectrometric signal that derives from a chromatographic elution profile of a sample compound.

The synthetic best-fit curves may be of any suitable form; however, good results have been obtained by modeling each baseline-corrected peak by synthetic model curves having either a Gaussian, an exponentially modified Gaussian or a Gamma line shape or comprising a pair of Gaussian-type curves. Considering the synthetic best-fit identified curve to the $i^{th}$ peak as a function of time having the general form, $\mathcal{F}_i(t)$, then the compensation for the effects of the elution profile comprises multiplying the baseline-corrected signal intensities of ions associated with the peak by the inverse function, $\mathcal{F}_i^{-1}(t)$. In this case, the "ions associated with the peak" are just those precursor ions that are generated from the compound whose elution generates the $i^{th}$ peak and any product ions generated from these precursor ions.

Once the contributions from elution profiles have been compensated (if necessary), any remaining variation in the signal intensities of the associated ions may be correlated with the variation of the operational parameters imposed during the elution of the compound. By analysis of this remaining variation optimum values of the operational parameters may be determined. The determined optimum values may be compound-specific. Accordingly, a subsequent analysis of the variation of signals of one or more of the characteristic precursor ion types may be conducted, in subsequent Step 614, to separate the component variations and thereby determine optimum values of the varied operational parameters. The variation of each operational parameter may be either random or systematic, between limits. Systematic variation of a parameter may include any form of programmed variation such as either incremental stepping or continuous ramping of the parameter, in either an increasing or decreasing fashion. Systematic variation of a parameter may also include periodic variation of a parameter or repeated alternating of the parameter value between different values (e.g., between high and low values).

According to various embodiments in accordance with the present teachings, a mass spectral signal intensity of at least one characteristic product ion type that is generated by fragmentation (or other reaction) of a characteristic precursor ion type may also be detected during the elution of compound of interest during an optimization experiment (Step 612a or Step 612b). In such cases, the characteristic precursor ion type is first isolated and then passed into and through a fragmentation or reaction cell of the mass spectrometer system within which the characteristic product ion type (or types) are generated. The product ion types are then delivered to a mass analyzer for analysis and signal detection. Multiple different precursor ion types may be fragmented in this fashion so as to produce multiple generations of product ions during the course of an optimization experiment. If a compound of interest generates more than one characteristic precursor ion type or if different compounds of interest co-elute, then the isolations and fragmentations of each of the various co-generated precursor ion types are cycled among these various precursor ion types during the period of co-generation. For example, an isolation and fragmentation of a first precursor ion type, together with the detection of the product ion types generated from the first precursor ion type will subsequently be followed by isolation and fragmentation of a second precursor ion type and detection of its product ion types, and so on.

In Step 614, the variations of the detected mass spectral signal intensities of ions—either precursor ions or product ions or both—corresponding to each analyte compound of interest are analyzed so as to determine the amount of signal intensity variation that is attributable to the variation of parameters that were varied during mass spectral detection of the ions derived from the respective compound during its elution. In some embodiments, this analysis may include compensation for the variation of ion signal intensity that is attributable to the elution profile of the compound from which the ions are derived as described, for example by Eq. 2.

In accordance with the present teachings, one or more operational parameters of the mass spectrometer system may be caused to vary during the course of detection of product ions. One of the varied operational parameters may be a value of a collision energy imparted to precursor ions prior to and during their entry into a fragmentation cell. The value of the collision energy affects the number of product ions of each product ion type that are formed in the fragmentation cell through collisions with neutral gas molecules in the collision cell. Such collision energy variation causes a component of variation in the detected intensity of the signals of characteristic product ion types that would otherwise be absent, in the absence of the variation of collision energy. As previously described, the variation of the detected signal intensity may also include another component of variation relating to an elution profile. Accordingly, a subsequent analysis of the variation of signals of one or more of the characteristic product ion types may be conducted, in subsequent Step 614, to separate the component variations and thereby determine an optimum value of collision energy to be used with each characteristic precursor ion type. The variation of the collision energy may be either random or systematic, between limits. Systematic variation may include any form of programmed variation such as either incremental stepping or continuous ramping of the collision energy, in either an increasing or decreasing fashion. Systematic variation may also include periodic variation of the collision energy or repeated alternating of the collision energy value between different values (e.g., between high and low values).

The following discussion provides an example mathematical treatment of a procedure for determining a number of required optimization experiments in Step 604 of the method 600 discussed above. It is assumed that every mass spectrometer operation is associated with a corresponding incremental (and essentially non-varying) time that is required for performing the operation. For example, one may define a quantity, $$\Delta t_{s,\Delta(\frac{m}{z})},$$

representing a "scan time" required to obtain a mass spectrum within a certain mass-to-charge range. Likewise, one may define an "isolation time", $\Delta t_{iso}$, representing the time required to accumulate a sample of ions and to eliminate ions not within a desired m/z range, or a "fragmentation time", $\Delta t_{frag}$, representing a time required to fragment a sample of ions, etc. It is further assumed that one may define a characteristic time that represents a time required to perform a set of operations that are commonly performed together, as a related group of operations. For example, one may define a time, $\Delta t_{SRM}$, representing time required to perform the combined operations of accumulating ions, isolating a restricted m/z range of those ions, fragmenting the isolated ions and then analyzing for the presence of a certain type of fragment ion.

The following example mathematical treatment considers a special case in which it is assumed that all basic mass spectrometer operations may be characterized in terms of a single characteristic time, $\Delta t_{SRM}$, as defined above. Different experimental situations may require a more-complex treatment; however, the general principle remains unchanged. For this example, also let the quantity $w_i$ represent the peak width (in time) of a chromatographic peak corresponding to the elution of the $i^{th}$ compound of interest. The peak width, $w_i$, may be defined, in the conventional sense, as "full-width at half maximum" or according to some other rule. As noted above, for optimization experiments in accordance with the present teachings, measurement efficiency and accuracy may be adequately balanced when the peak width is defined as "full-width at 20% maximum". Further, let the integer $s_{min}$ be an experimental constant (for example, $s_{min}=100$) that describes the number of times that the intensity of any ion species must be measured during variation of an experimental parameter in order to confidently determine the functional dependence of the intensity on the parameter. In the absence of any co-elution, the time, $\tau_i$, required to measure the full effect of a parameter variation on a mass spectral intensity of an ion species derived from the $i^{th}$ compound of interest will be simply $\tau_i=s_{min}\Delta t_{SRM}$. This equation assumes that only one characteristic ion species of each compound of interest is measured during the optimization experiments (e.g., only a single MS/MS measurement per compound). The present analysis can be generalized, by one of ordinary skill in the art, to cases in which this assumption is not true. For example if $b_i$ different MS/MS measurements are performed, with fragmentation of different respective precursor ions, on ions derived from the $i^{th}$ compound of interest, then the above equation may be generalized to $\tau_i=b_is_{min}\Delta t_{SRM}$. The parameter b may not be constant for all compounds of interest.

Under the assumption of one characteristic ion species per compound of interest, then it may be generally understood that the measurement speed of modern mass spectrometers is such that, without co-elution, $\tau_i<w_i$. However, if one or more additional compounds of interest are co-eluting at the same time that such measurements are being made, then the required time, $\tau_i$, will necessarily be greater, since the mass spectral measurements must cycle through measurements of ion species characteristic of each respective co-eluting compound. Depending on the number of co-eluting compounds (determined from survey step 601 of method 600), there may be some situations for which it would be true that $\tau_i>w_i$ if one were to attempt to optimize all experimental parameters as they pertain to each and every compound of interest in a single optimization experiment (step 612). In such situations, additional optimization experiments must be scheduled.

Still with reference to Step 604, a formalism is required for counting the number of possibly co-eluting compounds of interest at any particular retention time, t. Therefore, let the presence of a compound of interest (the $i^{th}$ compound of interest) in an eluate at a particular time t be denoted by the Boolean-valued function of time $a_i(t)$. When t falls between the start time, $t_{0i}$, and stop time, $t_{fi}$, for the compound elution window, the function equals 1, otherwise it is 0.

$$a_i(t) = \begin{cases} 1 & t_{0i} \le t < t_{fi} \\ 0 & \text{otherwise} \end{cases} \quad \text{Eq. 3}$$

Further, let the integer-valued function $n_i(t)$ be a function that counts the number of other compounds of interest which co-elute with compound $a_i$ at any time, t.

$$n_i(t) = \Sigma_j a_j(t) \quad (j \neq i) \qquad \text{Eq. 4}$$

At starting time $t_{0i}$, the incremental time $\Delta \tau_i(t_0)$ ($\equiv \Delta \tau_{i,0}$), between successive mass spectral measurements pertaining to the $i^{th}$ compound of interest is then given by $$\Delta \tau_{i,0} = [b_i + \Sigma_{j0} b_{j0}] \Delta t_{SRM} \qquad \text{Eq. 5a}$$

where the index, j0, is taken over all just those compounds of interest, $a_j$, that co-elute with the $i^{th}$ such compound at time $t_0$ such that the summation consists of $n_i(t_0)$ terms. Then, in recursive fashion, at time $t = t_{0i} + \Delta \tau_{i,0}$, the next incremental time, $\Delta \tau_i(t_{0i} + \Delta \tau_{i,0})$ ($\equiv \Delta t_{i,1}$) is given by $$\Delta \tau_{i,1} = [b_i + \Sigma_{j1} b_{j1}] \Delta t_{SRM} \qquad \text{Eq. 5b}$$

where the index, j1, is now taken over all just those compounds of interest, $a_j$, that co-elute with the $i^{th}$ such compound at the new time, $t = t_{0i} + \Delta \tau_{i,0}$, such that the summation consists of $n_i(t_{0i} + \Delta \tau_{i,0})$ terms, and so on. The total time, $\tau_i$, that would be required to make all $s_{min}$ measurements is then given by the following sum consisting of $s_{min}$ terms, in which $m = s_{min} - 1$ $$\tau_i = \Delta \tau_{i,0} + \Delta \tau_{i,1} + \ldots + \Delta \tau_{i,k} + \ldots + \Delta \tau_{i,m} \qquad \text{Eq. 6}$$

If $\tau_i > w_i$, then the investigation of at least one of the co-eluting compounds of interest should be moved to a separate optimization experiment.

Figures 7A, 7B:
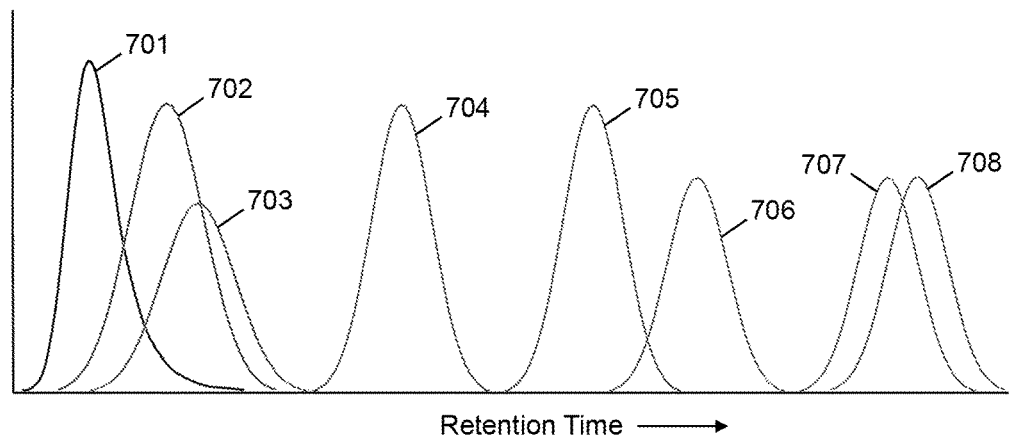
FIG. 7A is a set of hypothetical ion chromatograms depicting the relative timing of the elution of compounds as may be determined by a survey spectrum in accordance with the present teachings.
FIG. 7B is a schematic hypothetical depiction of a pair of tables showing a tabulation of pairs of compounds which would co-elute in tentative first and second optimization experiments if all of the compounds of FIG. 7A were analyzed in the first optimization experiment.

FIGS. 7A-7H schematically depict an example of steps that may be carried out in the distribution of compounds of interest (Step 604 of the method 600) among a plurality of optimization experiments in accordance with the present teachings. FIG. 7A is a set of hypothetical ion chromatograms depicting the relative timing of the elution of the compounds (eight such compounds in this example) as may be determined by a survey spectrum (Step 601 of the method 600) in accordance with the present teachings. The various compound elutions are represented by curves (i.e., "peaks") 701-708. Peak 701 corresponds to the compound of interest $a_1$ (i.e., compound $a_i$ where i=1); peak 702 corresponds to compound of interest $a_2$ (i.e., compound $a_i$ where i=2); etc. The topmost table of FIG. 7B shows a tabulation (with symbols "X") of just those pairs of compounds which would co-elute in tentative single optimization experiment if all of the analyses were scheduled in the single experiment and none of the analyses were scheduled for a second optimization experiment. The labels in the top row and in the leftmost column of the topmost table are all non-empty, thereby indicating that all compounds of interest are considered to be present in this tentative first optimization experiment. The lowermost table of FIG. 7B relates to the tentative second optimization experiment and is empty because none of the compound analyses have yet been scheduled to be performed in the second experiment.

First considering the topmost labeled row (i=1) of the topmost table of FIG. 7B, the required time, $\tau_1$, is calculated using Eq. 6. For this example, it is assumed that the calculated time, $\tau_1$, is greater than the available time, $w_i$, because peak 701 overlaps with both peak 702 and peak 703. Therefore, the scheduling of the analysis of compound $a_1$ is changed, as schematically depicted in FIGS. 7C-7D, such that the compound is analyzed in the second experiment.

Figures 7C, 7D:
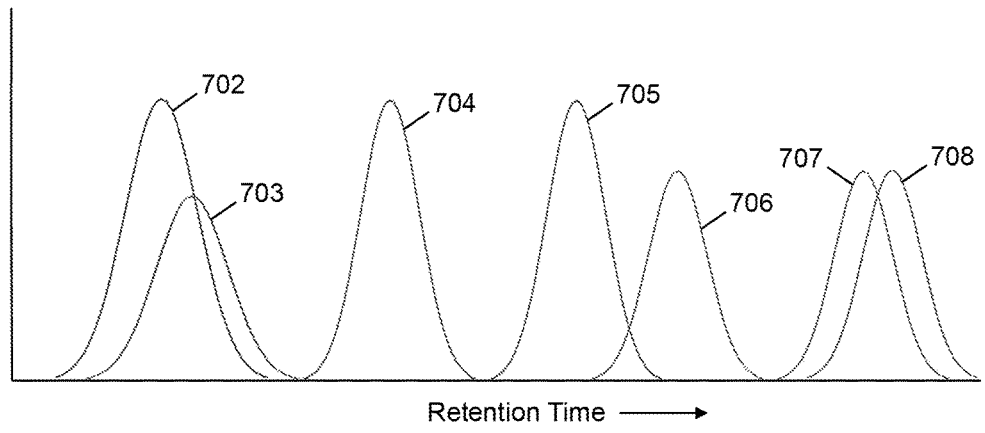
FIG. 7C is a set of hypothetical ion chromatograms depicting the relative timing of the elution of the compounds of FIG. 7A in a tentative first experiment, after redistribution of the analysis of one of the compounds to a second optimization experiment.
FIG. 7D is a pair of tables showing a tabulation of pairs of compounds which would co-elute in tentative first and second optimization experiments after redistribution of the analysis of one of the compounds to the second optimization experiment.

FIG. 7C shows the elution times of the remaining seven compounds scheduled for the first experiment, after the removal of compound $a_1$. Therefore, the next labeled not-previously-considered row (i=2) of the topmost table of FIG. 7D is considered so as to calculate the required time, $\tau_2$, using Eq. 6. In this step, only the co-elution between compound $a_1$ and compound $a_2$ is considered, since the elution of compound $a_1$ was re-scheduled for the second optimization experiment. For this example, it is assumed that the calculated time, $\tau_2$, is greater than the available time, $w_2$, because of the extensive overlap between peak 702 and peak 703. Accordingly, the scheduled analysis of one or the other of the compounds $a_2$ and $a_3$ must be moved to a different optimization experiment.

Figures 7E, 7F:
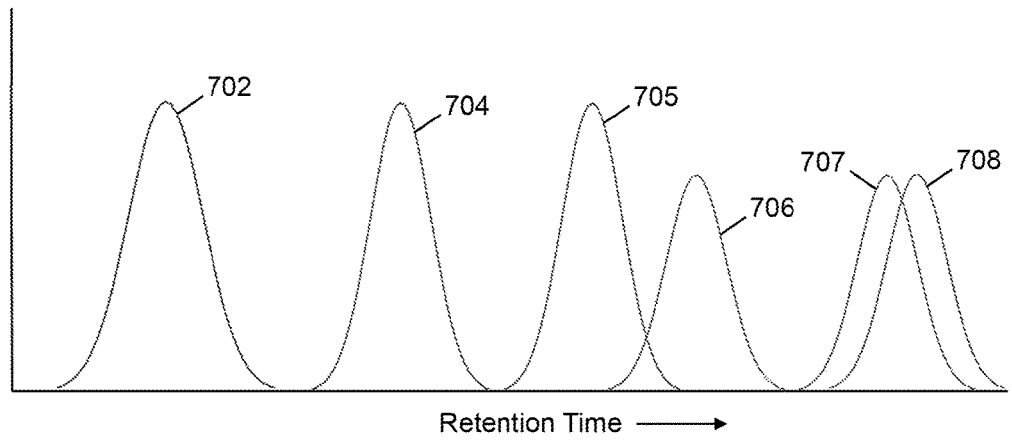
FIG. 7E is a set of hypothetical ion chromatograms depicting the relative timing of the elution of the compounds of FIG. 7A in a tentative first experiment, after redistribution of the analysis of two of the compounds to a second optimization experiment.
FIG. 7F is a pair of tables showing a tabulation of pairs of compounds which would co-elute in tentative first and second optimization experiments after redistribution of the analysis of two of the compounds to the second optimization experiment.

In this example, the scheduled analysis of compound $a_3$ is tentatively moved to the second optimization experiment as shown in FIGS. 7E and 7F. At this point, the co-elution that is indicated in the second optimization experiment ("X" marks in the lowermost table of FIG. 7F) must be considered so as to confirm that, under the scheduling of the second experiment, $\tau_1 \leq w_1$ and, if this expression is true, also that $\tau_3 \leq w_3$. In this example, it is assumed that both of these expressions are true because of the minimal overlap between peak 701 and peak 703. If either $\tau_1 > w_1$ or $\tau_3 > w_3$, then the scheduled analysis of either compound $a_1$ or compound $a_3$ must be moved to a third optimization experiment.

Figures 7G, 7H:
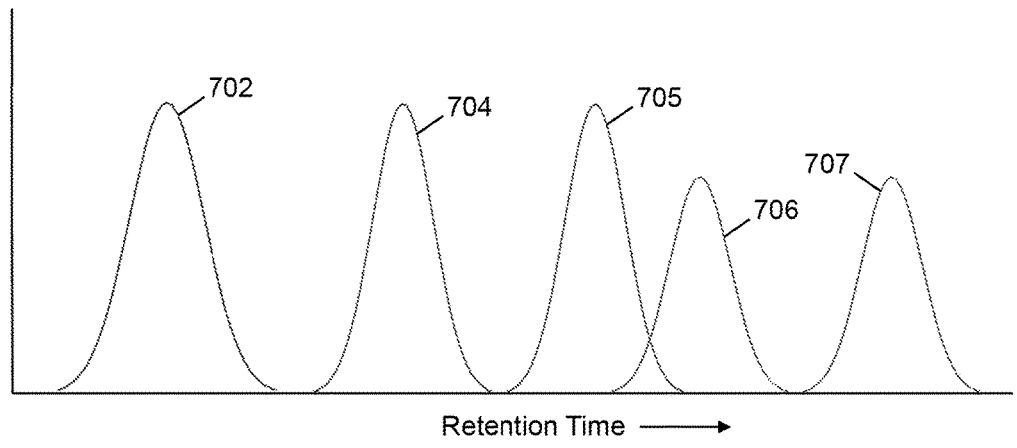
FIG. 7G is a set of hypothetical ion chromatograms depicting the relative timing of the elution of the compounds of FIG. 7A in a tentative first experiment, after redistribution of the analysis of three of the compounds to a second optimization experiment.
FIG. 7H is a pair of tables showing a tabulation of pairs of compounds which would co-elute in tentative first and second optimization experiments after redistribution of the analysis of three of the compounds to the second optimization experiment.

With the analyses of compounds $a_1$ and $a_3$ moved from the first to the second optimization experiment, the elution periods in the first experiment are as shown in FIG. 7E. Consideration next passes to the co-elution between compound $a_5$ and compound $a_6$ in the first experiment. If either $\tau_5 > w_5$ or $\tau_6 > w_6$, then the scheduled analysis of either compound $a_5$ or compound $a_6$ must be moved to the second optimization experiment. However, in this example it is assumed that neither such condition is true. Therefore, consideration next passes to the co-elution between compound $a_7$ and compound $a_8$ in the first experiment. In this example, it is assumed that both $\tau_7 > w_7$ or $\tau_8 > w_8$, because of the extensive overlap between peak 707 and peak 707. Accordingly, the analysis of compound $a_8$ is moved to the second optimization experiment. The two tables of FIG. 7H show the final distribution of analyte compound analyses between the two optimization experiments and FIG. 7G illustrates the elution profiles of the compounds that are scheduled to be analyzed in the first such optimization experiment.

Although the above procedure can be used to schedule compound analyses within or in accordance with a plurality of optimization experiments such that sufficient time is available, for each compound, to perform the full number of required measurements of the respective compound, it does not guarantee against scheduling too many experiments. For efficiency, it is desired to able to schedule an optimal number of optimization experiments—that is, the minimum number of experiments that provides sufficient time for the analysis of each and every compound of interest. To provide an approach as to how this an optimal number of experiments may be determined, let an optimization experiment, e, be represented by the set of compounds analyzed therein, that is, let $e = \{a_1, a_2, \ldots, a_k\}$. Then, the maximum co-elution within the experiment, e, is given by $$N(e) = \max_{i,t} n_i(t), i \in [1, k] \qquad \text{. Eq. 7}$$

Thus, the problem of determining the best set of optimization experiments, $\mathcal{S} = \{e_1, e_2, \ldots, e_m\}$, is found by distributing the compounds between sets to minimize the value of the maximum co-elution. The maximum density for the set, $\mathcal{S}$, of experiments is then, $$D(S) = \max_j N(e_j), \, j \in [1, m] \qquad \text{Eq. 8}$$

However, the maximum allowable density, $d_{max}$, is given by the peak widths, $w_i$ the characteristic time (e.g., $\Delta t_{SRM}$), and the number of scans, $s_{min}$, needed for an optimization.

$$d_{max} = \frac{\min_i w_i}{\Delta t_{SRM} s_{min}} \qquad \text{Eq. 7}$$

Finally, the optimization problem is written as follows:

$$\operatorname*{argmin}_S D(S) \qquad \text{Eq. 8}$$
$$D(S) < d_{max}$$

This expression is to be read, in words, as follows: an optimization that finds the argument, $S$, that minimizes the function $D(S)$, such that $D(S)$ is less than $d_{max}$. One accepted way of solving this problem is with evolutionary algorithms. Accordingly, another method for scheduling compounds among optimization experiments is here described. In the method, $D(S)$ is first determined for one experiment. If $D(S) > d_{max}$, then an additional optimization experiment is scheduled, where the components are distributed randomly between the two experiments. The components can be shuffled around between the experiments using an evolutionary algorithm at this point, or not. Then $D(S)$ is computed again, and if it is still true that $D(S) > d_{max}$, then the process is repeated in this fashion. These steps are iterated until $D(S) < d_{max}$.

In conclusion, methods for performing MS parameter optimization with time varying analyte compound concentration has been disclosed. This method fits into a larger optimization workflow, that creates a series of optimization experiments where analyte compounds are spaced out enough according to their retention times such that optimization can be performed. The discussion included in this application is intended to serve as a basic description. Although the invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the scope and essence of the invention. Neither the description nor the terminology is intended to limit the scope of the invention. Any patents, patent applications, patent application publications or other literature mentioned herein are hereby incorporated by reference herein in their respective entirety as if fully set forth herein.

What is claimed is:

1. A method for determining optimal values of a mass spectral operating parameter for use in analyzing each of a plurality of compounds by mass spectrometry comprising:
    performing a survey liquid chromatography/mass spectrometry (LCMS) experiment, said experiment comprising a plurality of mass spectral measurements of each of at least one characteristic ion species of each respective compound as said each respective compound is introduced into a mass spectrometer during its elution from a chromatograph;
    determining a respective elution time window of each characteristic ion species, based on the plurality of mass spectral measurements;
    planning a minimum number of subsequent chromatography/mass spectrometry (LCMS) experiments, each subsequent LCMS experiment performed on a mixture consisting of a respective subset of the plurality of compounds, wherein the subset compounds of each subsequent experiment are chosen based on the determined elution time windows;
    performing each of the subsequent LCMS experiments, wherein each subsequent experiment comprises a plurality of mass spectral measurements of each of the at least one characteristic ion species of each subset compound of said each subsequent experiment as said each respective subset compound is introduced into the mass spectrometer during its elution from the chromatograph, wherein, for each characteristic ion species, the operational parameter is caused to vary between successive mass spectral measurements of the said each characteristic ion species;
    calculating, for each characteristic ion species, a corrected intensity of at least a portion of the plurality of mass spectral measurements of said each characteristic ion species measured during the planned subsequent LCMS experiments, based on a best-fit synthetic model curve that relates to the time variation of the elution of the respective corresponding compound quantity; and
    determining the optimal values of the mass spectral operating parameter from analyses of the variation of the corrected intensities with respect to variation of the operational parameter.

2. A method for determining optimal values of a mass spectral operating parameter as recited in claim 1, wherein the at least one best-fit synthetic model curve is generated from elution profiles measured and recorded during the survey LCMS experiment.

3. A method for determining optimal values of a mass spectral operating parameter as recited in claim 1, wherein a best-fit synthetic model curve relating to the time variation of a respective corresponding compound quantity is generated from a subset of the plurality of mass spectral measurements acquired of the characteristic ion species corresponding to said respective compound during a subsequent LCMS experiment, wherein each mass spectral measurement composing the subset is acquired when the operational parameter is set at a non-variable control value.

4. A method for determining optimal values of a mass spectral operating parameter as recited in claim 1, wherein each best-fit synthetic model curve is generated from a respective ion chromatogram determined from the survey LCMS experiment.

5. A method for determining optimal values of a mass spectral operating parameter as recited in claim 1,
    wherein each subset is a unique subset of the plurality of compounds, and
    wherein the subset compounds of each planned subsequent LCMS experiment are chosen such that at least a predetermined minimum number, $s_{min}$, of mass spectral measurements are acquired of each characteristic ion species of each subset compound, during the acquiring of the plurality of mass spectral measurements of each characteristic ion species of each subset compound during the performing of said each planned subsequent LCMS experiment.

6. A method for determining optimal values of a mass spectral operating parameter as recited in claim 1, wherein one or more of the characteristic ion species are fragment ions whose m/z ratios are determined during the survey LCMS experiment.

7. A method for determining optimal values of a mass spectral operating parameter as recited in claim 1, wherein each best-fit synthetic model curve is generated automatically, in the absence of fitting parameter input by a user.

8. A method for determining optimal values of a mass spectral operating parameter as recited in claim 1, wherein the operational parameter is caused to vary randomly between successive mass spectral measurements of a characteristic ion species during the performing of the planned subsequent LCMS experiments.

9. A method for determining optimal values of a mass spectral operating parameter as recited in claim 1, wherein the calculating of the corrected intensity of at least a portion of the plurality of mass spectral measurements of a characteristic ion species obtained during the performing of the planned subsequent LCMS experiments is performed on a portion of the plurality of said mass spectral measurements of the characteristic ion species for which a measured intensity is greater than twenty percent of a maximum intensity measured during the acquiring of the plurality of mass spectral measurements of the characteristic ion species obtained during the performing of the planned subsequent LCMS experiments.

10. A method for determining optimal values of a mass spectral operating parameter as recited in claim 1, wherein the operational parameter is collision energy.

11. A method for determining optimal values of a mass spectral operating parameter as recited in claim 1, wherein the operational parameter is a magnitude of a Radio Frequency voltage applied to an ion guiding component of the mass spectrometer.

* * * * *

UNITED STATES PATENT AND TRADEMARK OFFICE
CERTIFICATE OF CORRECTION

PATENT NO. : 10,139,379 B2
APPLICATION NO. : 15/189953
DATED : November 27, 2018
INVENTOR(S) : Philip M. Remes It is certified that error appears in the above-identified patent and that said Letters Patent is hereby corrected as shown below:

In the Claims

Claim 1, Column 26, Line 32:
Replace "the respective corresponding compound quantity; and"
With --the respective corresponding compound; and--

Signed and Sealed this
Twenty-seventh Day of August, 2019

Andrei Iancu
*Director of the United States Patent and Trademark Office*